United States Patent
Venter et al.

(10) Patent No.: US 12,011,467 B2
(45) Date of Patent: Jun. 18, 2024

(54) BACTERIAL FORMULATION

(71) Applicant: J. Craig Venter Institute, Inc., La Jolla, CA (US)

(72) Inventors: Craig Venter, La Jolla, CA (US); Karen Nelson, Sandy Spring, MD (US); Derrick E. Fouts, Annapolis, MD (US); Weizhong Li, San Diego, CA (US); Aubrie O'Rourke, La Jolla, CA (US); Manolito Torralba, Lanham, MD (US)

(73) Assignee: J. Craig Venter Institute, Inc., La Jolla, CA (US)

( * ) Notice: Subject to any disclaimer, the term of this patent is extended or adjusted under 35 U.S.C. 154(b) by 0 days.

(21) Appl. No.: 17/663,634

(22) Filed: May 16, 2022

(65) Prior Publication Data
US 2023/0017769 A1   Jan. 19, 2023

Related U.S. Application Data

(60) Provisional application No. 63/190,142, filed on May 18, 2021.

(51) Int. Cl.
| | | |
|---|---|---|
| A61K 35/741 | (2015.01) | |
| A61K 35/745 | (2015.01) | |
| A61K 45/06 | (2006.01) | |
| C12N 1/20 | (2006.01) | |
| C12R 1/01 | (2006.01) | |

(52) U.S. Cl.
CPC .......... *A61K 35/741* (2013.01); *A61K 35/745* (2013.01); *A61K 45/06* (2013.01); *C12N 1/205* (2021.05); *C12R 2001/01* (2021.05)

(58) Field of Classification Search
CPC .... A61K 35/741; A61K 35/745; C12N 1/205; C12R 2001/01
See application file for complete search history.

(56) References Cited

U.S. PATENT DOCUMENTS

| | | | |
|---|---|---|---|
| 6,696,057 B1 | 2/2004 | Bojrab | |
| 8,906,668 B2* | 12/2014 | Henn | A23L 33/135 |
| | | | 435/252.4 |
| 9,314,489 B2 | 4/2016 | Kelly et al. | |
| 9,463,208 B2 | 10/2016 | Hlavka | |
| 9,585,920 B2 | 3/2017 | Kovarik et al. | |
| 9,610,308 B2 | 4/2017 | Borody | |
| 9,669,059 B2 | 6/2017 | Wang | |
| 10,052,353 B2 | 8/2018 | Honda et al. | |
| 2016/0271189 A1* | 9/2016 | Cutcliffe | A61K 31/715 |
| 2017/0065647 A1* | 3/2017 | Kim | A61K 35/747 |
| 2017/0304374 A1 | 10/2017 | Honig et al. | |
| 2018/0221286 A1 | 8/2018 | Kabadi et al. | |
| 2018/0353554 A1 | 12/2018 | Henn et al. | |
| 2022/0047647 A1* | 2/2022 | Honda | C12N 1/205 |

FOREIGN PATENT DOCUMENTS

| | | | | |
|---|---|---|---|---|
| WO | WO 2018/075886 A1 | 4/2018 | | |
| WO | WO-2020054728 A1 * | 3/2020 | | A61K 35/74 |

OTHER PUBLICATIONS

Duranti et al. Evaluation of genetic diversity among strains of the human gut commensal Bifidobacterium adolescentis, Scientific Reports 6:23971, 2016, DOI: 10.1038/srep23971 (Year: 2016).*

Seq ID No. 10—ATCC 15703 Alignment (Altschul, S.F., Gish, W., Miller, W., Myers, E.W. & Lipman, D.J. (1990) "Basic local alignment search tool." J. Mol. Biol. 215:403-410), search performed Mar. 1, 2023. (Year: 2023).*

Basholli-Salihu, et al., "Effect of lyoprotectants on β-glucosidase activity and viability of *Bifidobacterium infantis* after freeze-drying and storage in milk and low pH juices." LWT—Food Science and Technology 57 (2014) 276-282.

* cited by examiner

*Primary Examiner* — Soren Harward
*Assistant Examiner* — Alexander M Duryee
(74) *Attorney, Agent, or Firm* — Knobbe, Martens, Olson & Bear, LLP

(57) ABSTRACT

Aspects of the present invention relate to compositions of bacterial isolates with probiotic activity. Aspects of the present invention also relate to compositions and methods that may confer health benefits to subjects in need thereof. This may be accomplished by administering to the subject an effective amount of the microorganism isolates and may include also administering an effective amount of a prebiotic, stabilizer, antibacterial agent, antifungal agent, and/or media component. Probiotic compositions may also be in combination with a suitable delivery system, such as a food product or a beverage, a food or beverage compositions, a food or beverage supplement or adjuvant.

22 Claims, No Drawings
Specification includes a Sequence Listing.

```
                             SEQUENCE LISTING

<160> NUMBER OF SEQ ID NOS: 10

<210> SEQ ID NO 1
<211> LENGTH: 1392
<212> TYPE: DNA
<213> ORGANISM: Bacteroides isolate LJ00115
<220> FEATURE:
<221> NAME/KEY: variation
<222> LOCATION: (1385)...(1385)
<223> OTHER INFORMATION: N can be any nucleotide
<220> FEATURE:
<221> NAME/KEY: variation
<222> LOCATION: (5)...(5)
<223> OTHER INFORMATION: N can be any nucleotide

<400> SEQUENCE: 1
gctcntgcgg ttacgtactt caggtacccc cggctttcat ggcttgacgg gcggtgtgta      60
caaggcccgg gaacgtattc accgcgccat ggctgatgcg cgattactag cgaatccagc     120
ttcacgaagt cgggttgcag acttcgatcc gaactgagag aggcttttgg gattagcatc     180
ctgtcaccag gtagcggcct tctgtacccc ccattgtaac acgtgtgtag ccccggacgt     240
aagggccgtg ctgatttgac gtcatcccca ccttcctcac atcttacgac ggcagtctct     300
ccagagtcct cagcatgacc tgttagtaac tgaagataag ggttgcgctc gttatggcac     360
ttaagccgac acctcacggc acgagctgac gacaaccatg cagcaccttc acatttgtct     420
tacgactata ctgtttccaa tatattcaaa tgcaatttaa gcccgggtaa ggttcctcgc     480
gtatcatcga attaaaccac atgttcctcc gcttgtgcgg gcccccgtca attcctttga     540
gtttcaccgt tgccggcgta ctccccaggt ggaatactta atgctttcgc ttggccgctt     600
actgtatatc gcaaacagcg agtattcatc gtttactgtg tggactacca gggtatctaa     660
tcctgtttga tacccacact ttcgagcatc agtgtcagtt gcagtccagt gagctgcctt     720
cgcaatcgga gttcttcgtg atatctaagc atttcaccgc tacaccacga attccgccca     780
```

```
cctctactgt actcaagaca gccagtatca actgcaattt tacgcttgag ccgcaaactt    840
tcacaactga cttaactgtc cacctacgct ccctttaaac ccaataaatc cggataacgc    900
tcggatcctc cgtattaccg cggctgctgg cacggagtta gccgatcctt attcatatgg    960
tacatacaaa aatccacacg tggaccactt tattcccata taaagaagt ttacaaccca   1020 tagggcagtc atccttcacg ctacttggct ggttcagact ctcgtccatt gaccaatatt   1080
cctcactgct gcctcccgta ggagtttgga ccgtgtctca gttccaatgt ggggggacctt  1140 cctctcagaa cccctatcca tcgaaggttt ggtgggccgt taccccacca actgcctaat   1200
ggaacgcatc cccatcgata accgaaattc tttaataatc aaaccatgcg gttctattat   1260
gccatcgggt attaatcttt ctttcgaaag gctatccccg agttatcggc aggttggata   1320
cgtgttactc acccgtgcgc cggtcgccat ctccagtttg caagcaaact ggaatgctgc   1380
ccctngactg ca                                                       1392

<210> SEQ ID NO 2
<211> LENGTH: 797
<212> TYPE: DNA
<213> ORGANISM: Odoribacter isolate LJ00541
<220> FEATURE:
<221> NAME/KEY: variation
<222> LOCATION: (11)...(11)
<223> OTHER INFORMATION: N can be any nucleotide

<400> SEQUENCE: 2
tctcgcggtc ncgatcttca ggtactcccg gcttccatgg cttgacgggc ggtgtgtaca     60
aggcccggga acgtattcac cgcgccatgg ctgatgcgcg attactagcg aatccaactt    120
cgtggagtcg ggttgcagac tccagtccga actacgaccg gctttagaga ttggcatcca    180
gtcacctggt agcggccctc tgtaccggcc attgtaacac gtgtgtggcc ccgggtgtaa    240
gggccgtgct gatttgacgt catccccgcc ttcctcgcac cttacggtgg cagtctcgac    300
agagtgcacg gccgaaccgt tggcaactgg cgatagggt tgcgctcgtt atgggactta    360
acccgacacc tcacggcacg agctgacgac aaccatgcag caccttgtga gaggctccga    420
agagaagaac gatttctcgc tcatgcatcc cacatttaaa cccgggtaag gttcctcgcg    480
tatcatcgaa ttaaaccaca tgttcctccg cttgtgcggg ccccgtcaa ttcctttgag    540 tttcatcgtt gccgacgtac tccccaggtg gctcacttaa tactttcgct tgaacccgga    600
cggtgtatcg cccagatcca gtgagcatcg tttacggcgt ggactaccag ggtatctaat    660
cctgttcgct acccacgctc tcgcgcatca gcgtcagata aaggctggga agctgccttc    720
gctatcgggg ttccaagtga tatctatgca tttcaccgct acttcacttg ttccgcctcc    780
ctcgacttct ctctagg                                                  797

<210> SEQ ID NO 3
<211> LENGTH: 576
<212> TYPE: DNA
<213> ORGANISM: Bacteroides isolate PRB03A2_ANA_TSB_B11
<220> FEATURE:
<221> NAME/KEY: variation
<222> LOCATION: (301)...(301)
<223> OTHER INFORMATION: N can be any nucleotide

<400> SEQUENCE: 3
cagtcgaggg gcagcatggt cttaacttgc taaggccgat ggcgaccggc gcacgggtga     60
gtaacacgta tccaacctgc cgtctactct tggacagcct tctgaaagga agattaatac    120
```

-continued

| | |
|---|---|
| aagatggcat catgagttca catgttcaca tgattaaagg tattccggta gacgatgggg | 180 |
| atgcgttcca ttacatagta ggcggggtaa cggcccacct agtcttcgat ggataggggt | 240 |
| tctgagagga aggtcccca cattggaact gagacccggt ccaaactcct acgggaggca | 300 |
| ncagtgagga atattggtca atgggcgcag gcctgaacca accaagtaac gtgaaggatg | 360 |
| actgccctat gggttgtaaa cttcttttat aaaggaataa agtcgggtat gtatacccgt | 420 |
| ttgcatgtac tttatgaata aggatcggct aactccgtgc cagcagccgc ggtaatacgg | 480 |
| aggatccgag cgttatccgg atttattggg tttaaaggga gcgtagatgg atgtttaagt | 540 |
| cagttgtgaa agtttgcggc tcaaccgtaa aattgc | 576 |

<210> SEQ ID NO 4
<211> LENGTH: 530
<212> TYPE: DNA
<213> ORGANISM: Parabacteroides isolate PRB02A2_ANA_TSB_F6
<220> FEATURE:
<221> NAME/KEY: variation
<222> LOCATION: (301)...(301)
<223> OTHER INFORMATION: N can be any nucleotide
<220> FEATURE:
<221> NAME/KEY: variation
<222> LOCATION: (471)...(471)
<223> OTHER INFORMATION: N can be any nucleotide
<220> FEATURE:
<221> NAME/KEY: variation
<222> LOCATION: (511)...(511)
<223> OTHER INFORMATION: N can be any nucleotide
<220> FEATURE:
<221> NAME/KEY: variation
<222> LOCATION: (528)...(528)
<223> OTHER INFORMATION: N can be any nucleotide
<220> FEATURE:
<221> NAME/KEY: variation
<222> LOCATION: (515)...(515)
<223> OTHER INFORMATION: N can be any nucleotide

<400> SEQUENCE: 4

| | |
|---|---|
| tgggaatatt tgctaaagat tcatcgctga tatataggca tgcgttccat taggcagttg | 60 |
| gcggggtaac ggcccaccaa accgacgatg gatagggggtt ctgagaggaa ggtcccccac | 120 |
| attggtactg acacacggac caaactccta cgggaggcag cagtgaggaa tattggtcaa | 180 |
| tggccgagag gctgaaccac ccaagtcgcg tgagggatga aggttctatg gatcgtaaac | 240 |
| ctcttttata agggaataaa gtgacccacg tgtgggtttt tgtatgtacc ttatgaataa | 300 |
| ngatcggcta actccgtgcc agcagccgcg gtaatacgga agatccgagc gttatccgga | 360 |
| tttattgggt ttaaagggtg cgtaggcggt cttttaagtc agcggtgaaa gtctgtggct | 420 |
| caaccataaa attgccgttg aaactgggag gcttgagtat gtttgaggca ngcggaatgc | 480 |
| gtggtgtagc ggtgaaatgc atatatatca cgcanaaccc cgattgcnaa | 530 |

<210> SEQ ID NO 5
<211> LENGTH: 798
<212> TYPE: DNA
<213> ORGANISM: Bacteroides isolate PRB01A2_ANA_MRS_C7

<400> SEQUENCE: 5

| | |
|---|---|
| atgaagagtt tgatcctggc tcaggatgaa cgctagctac aggcttaaca catgcaagtc | 60 |
| gaggggcatc agggtgtagc aatacaccgc tggcgaccgg cgcacgggtg agtaacacgt | 120 |
| atccaacctg cccctttactc ggggatagcc tttcgaaaga aagattaata cccgatggta | 180 |
| taacatgacc tcctggtttt gttattaaag aatttcggta gaggatgggg atgcgttcca | 240 |
| ttaggcagtt ggcggggtaa cggcccacca aaccttcgat ggataggggt tctgagagga | 300 |

```
aggtccccca cattggaact gagacacggt ccaaactcct acgggaggca gcagtgagga    360
atattggtca tgggcgaga gcctgaacca gccaagtagc gtgaaggatg accgccctat     420
gggttgtaaa cttctttat atgggaataa agtgcagtat gtatactgtt ttgtatgtac     480
catacgaata aggatcggct aactccgtgc cagcagccgc ggtaatacgg aggatccgag    540
cgttatccgg atttattggg tttaaaggga gcgtaggtgg acatgtaagt cagttgtgaa    600
agtttgcggc tcaaccgtaa aattgcagtt gaaactgcgt gtcttgagta cagtagaggt    660
gggcggaatt cgtggtgtag cggtgaaatg cttagatatc acgaagaact ccgatcgcga    720
aggcaggtgt ccgggctgca actgacgctg aggctcgaaa gtgtgggtat caaacaggat    780
tagaaacccc agtagtcc                                                 798

<210> SEQ ID NO 6
<211> LENGTH: 601
<212> TYPE: DNA
<213> ORGANISM: Paraprevotella isolate LJ00262
<220> FEATURE:
<221> NAME/KEY: variation
<222> LOCATION: (1)...(1)
<223> OTHER INFORMATION: N can be any nucleotide

<400> SEQUENCE: 6
ntcgcggtca cggacttcag gcaccccgg ctttcatggc ttgacgggcg gtgtgtacaa      60
ggcccgggaa cgtattcacc gcgccatggc tgatgcgcga ttactagcga atccagcttc    120
gtggagtcgg gttgcagact ccagtccgaa ctgagagggg ttttagggat tggccgaccg    180
tcaccggaca gcggccctct gtacccccca ttgtaacacg tgtgtggccc cggacgtaag    240
ggccgtgctg atttgacgtc atccccacct tcctcgcatc ttacgatggc agtgtcccca    300
gagggcccgg cattacccga tggcaactgg ggagaagggt tgcgctcgtt atggcactta    360
agccgacacc tcacggcacg agctgacgac aaccatgcag caccttcaca ggagtcccga    420
aggaaagaat catctctgac tcatgcacct gcaattcaag cccgggtaag gttcctcgcg    480
tatcatcgaa ttaaaccaca tgttcctccg cttgtgcggg cccccgtcaa ttcctttgag    540
tttcaccgtt gccggcgtac tccccaggtg gaatgcttaa cgctttcgct tggccacgga    600
c                                                                   601

<210> SEQ ID NO 7
<211> LENGTH: 1357
<212> TYPE: DNA
<213> ORGANISM: Coprococcus isolate LJ00622

<400> SEQUENCE: 7
tgattcttcg gatgaagagg tttgtgactg agtggcggac gggtgagtaa cgcgtgggta     60
acctgcctca tacagggga taacagttag aaatgactgc taataccgca taagaccacg    120
gagccgcatg gctccgtggg aaaaactccg gtggtatgag atggacccgc gtctgattag    180
gtagttggtg gggtaacggc ctaccaagcc gacgatcagt agccgacctg agagggtgac    240
cggccacatt gggactgaga cacggcccaa actcctacgg gaggcagcag tggggaatat    300
tgcacaatgg gggaaaccct gatgcagcga cgccgcgtga gcgaagaagt atttcggtat    360
gtaaagctct atcagcaggg aagaaaatga cggtacctga ctaagaagca ccggctaaat    420
acgtgccagc agccgcggta atacgtatgg tgcaagcgtt atccggattt actgggtgta    480
aagggagcgt agacggctgt gtaagtctga agtgaaagcc cggggctcaa ccccgggact    540
```

| | |
|---|---|
| gctttggaaa ctatgcagct agagtgtcgg agaggtaagt ggaattccca gtgtagcggt | 600 |
| gaaatgcgta gatattggga ggaacaccag tggcgaaggc ggcttactgg acgatgactg | 660 |
| acgttgaggc tcgaaagcgt ggggagcaaa caggattaga taccctggta gtccacgccg | 720 |
| taaacgatga ctactaggtg tcggggagca aagctcttcg gtgccgcagc aaacgcaata | 780 |
| agtagtccac ctggggagta cgttcgcaag aatgaaactc aaaggaattg acggggaccc | 840 |
| gcacaagcgg tggagcatgt ggtttaattc gaagcaacgc gaagaacctt acctgctctt | 900 |
| gacatcccgg tgaccggcgt gtaatgacgc ttttcttcg gaacaccggt gacaggtggt | 960 |
| gcatggttgt cgtcagctcg tgtcgtgaga tgttgggtta agtcccgcaa cgagcgcaac | 1020 |
| ccttatcttc agtagccagc attttggatg ggcactctgg agagactgcc agggataacc | 1080 |
| tggaggaagg tggggatgac gtcaaatcat catgcccctt atgagcaggg ctacacacgt | 1140 |
| gctacaatgg cgtaaacaaa gggaagcgag cctgcgaggg taagcaaatc tcaaaaataa | 1200 |
| cgtctcagtt cggattgtag tctgcaactc gactacatga agctggaatc gctagtaatc | 1260 |
| gcgaatcagc atgtcgcggt gaatacgttc ccgggtcttg tacaccgc ccgtcacacc | 1320 |
| atgggagttg gtaacgcccg aagtcagtga cccaacc | 1357 |

```
<210> SEQ ID NO 8
<211> LENGTH: 421
<212> TYPE: DNA
<213> ORGANISM: Acidaminococcus isolate PRB01A2_ANA_GAM_C8

<400> SEQUENCE: 8
```

| | |
|---|---|
| tctccagcgc gtaatggcgg ggactcatag gagactgcca gggataactt ggaggaaggc | 60 |
| ggggatgacg tcaagtcatc atgccccttaa tgtcttgggc tacacacgta ctacaatggt | 120 |
| cggcaacaaa gggcagcgat accgcgaggt ggagcaaatc ccagaaaccc gaccccagtt | 180 |
| cggatcgtag gctgcaaccc gcctacgtga agttggaatc gctagtaatc gcaggtcagc | 240 |
| atactgcggt gaatacgttc ccgggccttg tacaccgcc cgtcacacc acgagagttt | 300 |
| gtaacacccg aagtcggtga ggtaaccatt taggagccag ccgcctaagg tgggatagat | 360 |
| gattggggtg aagtcgtaac aaggtagccg tatcggaagg tgcggctgga tcacctcctt | 420 |
| t | 421 |

```
<210> SEQ ID NO 9
<211> LENGTH: 315
<212> TYPE: DNA
<213> ORGANISM: Bifidobacterium isolate PRB02A2_ANA_TSB_A11
<220> FEATURE:
<221> NAME/KEY: variation
<222> LOCATION: (95)...(95)
<223> OTHER INFORMATION: N can be any nucleotide

<400> SEQUENCE: 9
```

| | |
|---|---|
| acgaggtccc atcccgttgt accggccatt gtagcatgcc tgaagccctg gaggtaaggg | 60 |
| gcatgatgat ctgacgtcat ccccaccttc ctccnagttg accccggcgg tccccgtga | 120 |
| gttcccaccc cgacgtgctg ggaacacagg gggagggttg cgctcgttgc gggacttaac | 180 |
| ccaacatctc acgacacgaa ctgacgacga ccatgcccca cctgtgaacc cggcccgaag | 240 |
| ggaaaccgta tctctacggt tgtcgggaac atgtcaagcc caggtaaggc tcttcgcgtt | 300 |
| gaattaaatt aatcc | 315 |

```
<210> SEQ ID NO 10
<211> LENGTH: 203
```

-continued

```
<212> TYPE: DNA
<213> ORGANISM: Bifidobacterium isolate PRB03A2_ANA_GAM.Ab_B11

<400> SEQUENCE: 10
ccaccggctt cgggtgctac ccactcttca tgacttgacg ggcggtgtgt acaaggcccg    60
ggaacgcatt caccgcggcg ttgctgatcc gcaattacta gcgactccgc cttcatggag   120
tcaggttgca cactccaatc caaactgaaa ccggttttaa aggatccgct ccccctcacg   180
aggtcgcatc ccgttgtacc ggc                                           203
```

BACTERIAL FORMULATION

CROSS-REFERENCE TO RELATED APPLICATIONS

This application claims the benefit of U.S. Provisional Application No. 63/190,142, filed May 18, 2021, which is hereby expressly incorporated by reference in its entirety.

FIELD OF THE INVENTION

Aspects of the present disclosure relate to bacterial isolates, methods of isolating and culturing said bacterial isolates, and methods of using these bacterial isolates to prevent, treat, or inhibit a disease. More specifically, certain features of the present disclosure concern beneficial bacterial strains, which can be provided to subjects to prevent, treat, or inhibit a disease or an adverse health condition associated with subjects that lack or have diminished amounts of said beneficial bacterial strains.

REFERENCE TO SEQUENCE LISTING

The present application is being filed along with a Sequence Listing in electronic format. The Sequence Listing is provided as a file entitled ReplacementSeqListing_JCVEN007A.TXT, which was created and last modified on Aug. 15, 2022 and is 10,983 bytes in size. The information in the electronic Sequence Listing is hereby incorporated by reference in its entirety.

BACKGROUND OF THE INVENTION

The microbiome is a genomic collection of the entire repertoire of microbiota of a subject. This microbiome includes beneficial and benign microbes, as well as harmful microbes. The human intestinal microbiota consists of trillions of microorganisms including 150-200 prevalent and 1000 less common bacterial species, harboring over 100-fold more genes than those present in the human genome. The gastrointestinal tract is the largest habitat of microbiota and is composed of predominantly bacteria, yet also contains archaea, protozoa, and viruses. The microbiota performs vital functions essential to health maintenance, including food processing, digestion of complex indigestible polysaccharides, synthesis of vitamins, and immune system functions. The microbiome also secretes bioactive metabolites with diverse functions, ranging from inhibition of pathogens, metabolism of toxic compounds, and the modulation of the metabolism of the host.

Dysbiosis is a state of imbalance in the composition or function of microbial taxa in a subject, which can lead to many diseases and adverse health conditions such as gastrointestinal and urogenital infections and the adverse health conditions associated therewith. The restoration of microbiotic homeostasis can be an effective therapeutic approach to attenuating dysbiosis-induced disease and several in the field have sought to address such dysbiosis-induced disease by administration of probiotics or fecal microbiota transplantation or both. Although the understanding of how the gut microbiota contributes to host health has progressed greatly, there remains a need for more approaches to address imbalances in the composition or function of microbial taxa of a subject.

SUMMARY OF THE INVENTION

Some aspects of the present disclosure relate to a composition comprising an isolate of *Bacteroides* designated LJ00115, wherein said isolate of *Bacteroides* comprises a 16S rRNA gene sequence encoding or corresponding to at least 95%, 96%, 97%, 98%, 99%, or 100% sequence identity of the rDNA sequence of SEQ ID NO: 1 or the complement thereof. This selected isolate of *Bacteroides* designated LJ00115 is deposited under the Budapest Treaty with the Westerdijk Fungal Biodiversity Institute, CBS collection, at Uppsalalaan 8, 3508 AD UTRECHT, The Netherlands under reference number CBS 149345. Accordingly, aspects of the invention concern compositions comprising the aforementioned *Bacteroides* isolate designated LJ00115 deposited under reference number CBS 149345, wherein said composition further comprises a prebiotic, stabilizer, antibacterial agent, antifungal agent, preservative, or media component, optionally wherein said composition or isolate is lyophilized, spray dried, or freeze-dried, optionally, wherein said isolate is inactivated, such as by heat inactivation and, optionally, wherein said composition or isolate is formulated in a powder, liquid, capsule, caplet, spray, or food, such as for oral delivery.

Some aspects of the present disclosure relate to a composition comprising an isolate of *Odoribacter* designated LJ00541, wherein said isolate of *Odoribacter* comprises a 16S rRNA gene sequence encoding or corresponding to at least 95%, 96%, 97%, 98%, 99%, or 100% sequence identity of the rDNA sequence of SEQ ID NO: 2 or the complement thereof. This selected isolate of *Odoribacter* designated LJ00541 is deposited under the Budapest Treaty with the Westerdijk Fungal Biodiversity Institute, CBS collection, at Uppsalalaan 8, 3508 AD UTRECHT, The Netherlands under reference number CBS 149346. Accordingly, aspects of the invention concern compositions comprising the aforementioned *Odoribacter* isolate designated LJ00541 deposited under reference number CBS 149346, wherein said composition further comprises a prebiotic, stabilizer, antibacterial agent, antifungal agent, preservative, or media component, optionally wherein said composition or isolate is lyophilized, spray dried, or freeze-dried, optionally, wherein said isolate is inactivated, such as by heat inactivation and, optionally, wherein said composition or isolate is formulated in a powder, liquid, capsule, caplet, spray, or food, such as for oral delivery.

Some aspects of the present disclosure relate to a composition comprising an isolate of *Bacteroides* designated PRB03A2_ANA_TSB_B11, wherein said isolate of *Bacteroides* comprises a 16S rRNA gene sequence encoding or corresponding to at least 95%, 96%, 97%, 98%, 99%, or 100% sequence identity of the rDNA sequence of SEQ ID NO: 3 or the complement thereof. This selected isolate of *Bacteroides* designated PRB03A2_ANA_TSB_B11 is deposited under the Budapest Treaty with the Westerdijk Fungal Biodiversity Institute, CBS collection, at Uppsalalaan 8, 3508 AD UTRECHT, The Netherlands under reference number CBS 149347. Accordingly, aspects of the invention concern compositions comprising the aforementioned *Bacteroides* isolate designated PRB03A2_ANA_TSB_B11 deposited under reference number CBS 149347, wherein said composition further comprises a prebiotic, stabilizer, antibacterial agent, antifungal agent, preservative, or media component, optionally wherein said composition or isolate is lyophilized, spray dried, or freeze-dried, optionally, wherein said isolate is inactivated, such as by heat inactivation and, optionally, wherein said composition or isolate is formulated in a powder, liquid, capsule, caplet, spray, or food, such as for oral delivery.

Some aspects of the present disclosure relate to a composition comprising an isolate of *Parabacteroides* designated PRB02A2_ANA_TSB_F6, wherein said isolate of *Parabacteroides* comprises a 16S rRNA gene sequence encoding or corresponding to at least 95%, 96%, 97%, 98%, 99%, or 100% sequence identity of the rDNA sequence of SEQ ID NO: 4 or the complement thereof. This selected isolate of *Parabacteroides* designated PRB02A2_ANA_TSB_F6 is deposited under the Budapest Treaty with the Westerdijk Fungal Biodiversity Institute, CBS collection, at Uppsalalaan 8, 3508 AD UTRECHT, The Netherlands under reference number CBS 149348. Accordingly, aspects of the invention concern compositions comprising the aforementioned *Parabacteroides* isolate designated PRB02A2_ANA_TSB_F6 deposited under reference number CBS 149348, wherein said composition further comprises a prebiotic, stabilizer, antibacterial agent, antifungal agent, preservative, or media component, optionally wherein said composition or isolate is lyophilized, spray dried, or freeze-dried, optionally, wherein said isolate is inactivated, such as by heat inactivation and, optionally, wherein said composition or isolate is formulated in a powder, liquid, capsule, caplet, spray, or food, such as for oral delivery Some aspects of the present disclosure relate to a composition comprising an isolate of *Bacteroides* designated PRB01A2_ANA_MRS_C7, wherein said isolate of *Bacteroides* comprises a 16S rRNA gene sequence encoding or corresponding to at least 95%, 96%, 97%, 98%, 99%, or 100% sequence identity of the rDNA sequence of SEQ ID NO: 5 or the complement thereof. This selected isolate of *Bacteroides* designated PRB01A2_ANA_MRS_C7 is deposited under the Budapest Treaty with the Westerdijk Fungal Biodiversity Institute, CBS collection, at Uppsalalaan 8, 3508 AD UTRECHT, The Netherlands under reference number CBS 149340. Accordingly, aspects of the invention concern compositions comprising the aforementioned *Bacteroides* isolate designated PRB01A2_ANA_MRS_C7 deposited under reference number CBS 149340, wherein said composition further comprises a prebiotic, stabilizer, antibacterial agent, antifungal agent, preservative, or media component, optionally wherein said composition or isolate is lyophilized, spray dried, or freeze-dried, optionally, wherein said isolate is inactivated, such as by heat inactivation and, optionally, wherein said composition or isolate is formulated in a powder, liquid, capsule, caplet, spray, or food, such as for oral delivery.

Some aspects of the present disclosure relate to a composition comprising an isolate of *Paraprevotella* designated LJ00262, wherein said isolate of *Paraprevotella* comprises a 16S rRNA gene sequence encoding or corresponding to at least 95%, 96%, 97%, 98%, 99%, or 100% sequence identity of the rDNA sequence of SEQ ID NO: 6 or the complement thereof. This selected isolate of *Paraprevotella* designated LJ00262 is deposited under the Budapest Treaty with the Westerdijk Fungal Biodiversity Institute, CBS collection, at Uppsalalaan 8, 3508 AD UTRECHT, The Netherlands under reference number CBS 149341. Accordingly, aspects of the invention concern compositions comprising the aforementioned *Paraprevotella* isolate designated LJ00262 deposited under reference number CBS 149341, wherein said composition further comprises a prebiotic, stabilizer, antibacterial agent, antifungal agent, preservative, or media component, optionally wherein said composition or isolate is lyophilized, spray dried, or freeze-dried, optionally, wherein said isolate is inactivated, such as by heat inactivation and, optionally, wherein said composition or isolate is formulated in a powder, liquid, capsule, caplet, spray, or food, such as for oral delivery.

Some aspects of the present disclosure relate to a composition comprising an isolate of *Coprococcus* designated LJ00622, wherein said isolate of *Coprococcus* comprises a 16S rRNA gene sequence encoding or corresponding to at least 99% or 100% sequence identity of the rDNA sequence of SEQ ID NO: 7 or the complement thereof. This selected isolate of *Coprococcus* designated LJ00622 is deposited under the Budapest Treaty with the Westerdijk Fungal Biodiversity Institute, CBS collection, at Uppsalalaan 8, 3508 AD UTRECHT, The Netherlands under reference number CBS 149349. Accordingly, aspects of the invention concern compositions comprising the aforementioned *Coprococcus* isolate designated LJ00622 deposited under reference number CBS 149349, wherein said composition further comprises a prebiotic, stabilizer, antibacterial agent, antifungal agent, preservative, or media component, optionally wherein said composition or isolate is lyophilized, spray dried, or freeze-dried, optionally, wherein said isolate is inactivated, such as by heat inactivation and, optionally, wherein said composition or isolate is formulated in a powder, liquid, capsule, caplet, spray, or food, such as for oral delivery.

Some aspects of the present disclosure relate to a composition comprising an isolate of *Acidaminococcus* designated PRB01A2_ANA_GAM_C8, wherein said isolate of *Acidaminococcus* comprises a 16S rRNA gene sequence encoding or corresponding to at least 95%, 96%, 97%, 98%, 99%, or 100% sequence identity of the rDNA sequence of SEQ ID NO: 8 or the complement thereof. This selected isolate of *Acidaminococcus* designated PRB01A2_ANA_GAM_C8 is deposited under the Budapest Treaty with the Westerdijk Fungal Biodiversity Institute, CBS collection, at Uppsalalaan 8, 3508 AD UTRECHT, The Netherlands under reference number CBS 149342. Accordingly, aspects of the invention concern compositions comprising the aforementioned *Acidaminococcus* isolate designated PRB01A2_ANA_GAM_C8 deposited under reference number CBS 149342, wherein said composition further comprises a prebiotic, stabilizer, antibacterial agent, antifungal agent, preservative, or media component, optionally wherein said composition or isolate is lyophilized, spray dried, or freeze-dried, optionally, wherein said isolate is inactivated, such as by heat inactivation and, optionally, wherein said composition or isolate is formulated in a powder, liquid, capsule, caplet, spray, or food, such as for oral delivery.

Some aspects of the present disclosure relate to a composition comprising an isolate of *Bifidobacterium* designated PRB02A2_ANA_TSB_A11, wherein said isolate of *Bifidobacterium* comprises a 16S rRNA gene sequence encoding or corresponding to at least 95%, 96%, 97%, 98%, 99%, or 100% sequence identity of the rDNA sequence of SEQ ID NO: 9 or the complement thereof. This selected isolate of *Bifidobacterium* designated PRB02A2_ANA_TSB_A11 is deposited under the Budapest Treaty with the Westerdijk Fungal Biodiversity Institute, CBS collection, at Uppsalalaan 8, 3508 AD UTRECHT, The Netherlands under reference number CBS 149343. Accordingly, aspects of the invention concern compositions comprising the aforementioned *Bifidobacterium* isolate designated PRB02A2_ANA_TSB_A11 deposited under reference number CBS 149343, wherein said composition further comprises a prebiotic, stabilizer, antibacterial agent, antifungal agent, preservative, or media component, optionally wherein said composition or isolate is lyophilized, spray dried, or freeze-dried, optionally, wherein said isolate is inactivated, such as by heat inactivation and, optionally, wherein said composition or isolate is formulated in a powder, liquid, capsule, caplet, spray, or food, such as for oral delivery.

Some aspects of the present disclosure relate to a composition comprising an isolate of *Bifidobacterium* designated PRB03A2_ANA_GAM.Ab_B11, wherein said isolate of *Bifidobacterium* comprises a 16S rRNA gene sequence encoding or corresponding to at least 95%, 96%, 97%, 98%, 99%, or 100% sequence identity of the rDNA sequence of SEQ ID NO: 10 or the complement thereof. This selected isolate of *Bifidobacterium* designated PRB03A2_ANA_GAM.Ab_B11 is deposited under the Budapest Treaty with the Westerdijk Fungal Biodiversity Institute, CBS collection, at Uppsalalaan 8, 3508 AD UTRECHT, The Netherlands under reference number CBS 149344. Accordingly, aspects of the invention concern compositions comprising the aforementioned *Bifidobacterium* isolate designated PRB03A2_ANA_GAM.Ab_B11 deposited under reference number CBS 149344, wherein said composition further comprises a prebiotic, stabilizer, antibacterial agent, antifungal agent, preservative, or media component, optionally wherein said composition or isolate is lyophilized, spray dried, or freeze-dried, optionally, wherein said isolate is inactivated, such as by heat inactivation and, optionally, wherein said composition or isolate is formulated in a powder, liquid, capsule, caplet, spray, or food, such as for oral delivery.

Additional embodiments concern compositions comprising at least one bacterial isolate comprising a 16S rRNA gene sequence encoding or corresponding to a sequence selected from any one or more of the aforementioned sequences or the complement thereof e.g., a 16S rRNA encoding or corresponding to any one or more of the rDNA sequences of SEQ ID NOS: 1-10 or the complement thereof or a sequence having at least 95%, 96%, 97%, 98%, or 99% sequence identity to any one or more of SEQ ID NOS: 1-10 or the complement thereof, such as anyone or more of the deposited strains above and, optionally, further comprising a prebiotic, stabilizer, antibacterial agent, antifungal agent, or media component. In some embodiments, the prebiotic is inulin, fructooligosaccharide, galactooligosaccharide, xylooligosaccharide, or lactulose. In some embodiments, the stabilizer comprises a sugar, a sugar alcohol, an amino acid, a lipid, or a fatty acid, or any combination thereof (e.g., raffinose, soybean oligosaccharides, fructooligosaccharides, galactooligosaccharides, galactosyl lactose, palatinose, lactulose, lactitol, xylitol, sorbitol, mannitol, trehalose, glucose, sucrose, fructose, maltose, milk, milk powders, whey, whey protein concentrates, casein, casein hydrolysates, lactoferrin, lactoperoxidase, lactoglobulins, glycomacropeptides, lacto-saccharides, lacto-lipids, or short chain fatty acids including acetic, propionic, butyric, isobutyric, valeric, isovaleric, or caproic acids). In some embodiments, the stabilizer is glucose, sucrose, trehalose, lactose, maltodextrin, polydextrose, dextran, fructose, oligofructose, cellulose, glycerol, adonitol, inositol, mannitol, sorbitol, gums, hydrolyzed protein, skim milk powder, milk powder, or gel beads, or any combination thereof. In some embodiments, the antibacterial agent is bacteriocin, amoxicillin, ampicillin, azithromycin, cefaclor, cefdinir, cefotaxime, ceftazidime, ceftriaxone, cefuroxime, cephalexin, cephalosporin, ciprofloxacin, clarithromycin, clavulanate, clindamycin, clotrimazole, dalbavancin, demeclocycline, dicloxacillin, doxycycline, eravacycline, erythromycin, fluconazole, furazolidone, lansoprazole, levofloxacin, lincomycin, metronidazole, minocycline, moxifloxacin, nitroimidazole, omadacycline, oritavancin, oxacillin, penem, penicillin, penicillin V potassium, rifabutin, sulfamethoxazole, sulfasalazine, telavancin, tetracycline, tinidazole, trimethoprim, an antimicrobial peptide, or vancomycin, or any combination thereof. In some embodiments, the antifungal agent is amphotericin B, clotrimazole, econazole, fluconazole, itraconazole, ketoconazole, miconazole, natamycin, nystatin, posaconazole, terconazole, terbinafine, or voriconazole, or any combination thereof. In some embodiments, the media component is selected from any one or more of the media components set forth in TABLE 2. In some embodiments, the media component further comprises agar. In some embodiments, the isolate or composition or both are lyophilized, spray dried, or freeze-dried. In some embodiments, the composition further comprises at least one additional bacterial population, wherein said at least one additional bacterial population comprises a 16S rRNA gene encoding or corresponding to an rDNA sequence selected from any one or more SEQ ID NOS: 1-10 or the complement thereof or any one or more of a sequence having at least 95%, 96%, 97%, 98%, or 99% sequence identity to any one or more of SEQ ID NOS: 1-10 or the complement thereof, such as anyone or more of the deposited strains above. In some embodiments, the composition comprises at least nine additional bacterial populations, wherein each of the at least nine additional bacterial populations comprises a 16S rRNA gene encoding or corresponding to a unique sequence selected from any one or more of rDNA sequence of SEQ ID NOS: 1-10 or the complement thereof or any one or more of a sequence having at least 95%, 96%, 97%, 98%, or 99% sequence identity to any one or more of SEQ ID NOS: 1-10 or the complement thereof such as anyone or more of the deposited strains above. In some embodiments, the composition further comprises at least one additional bacterial population selected from the bacteria set forth in TABLE 3. Each of these compositions may also contain any one or more of the aforementioned prebiotics, stabilizers, antibacterial agents, antifungal agents, or media components.

Further embodiments relate to methods of treating, ameliorating, preventing, or inhibiting a disease or a condition associated with a disease such as e.g., allergies, infection risk in the critically ill, sexually transmitted infections, acne, acute infectious diarrhea, acute respiratory tract infections, allergic rhinitis, Alzheimer's disease, antibiotic-associated diarrhea, atopic dermatitis, asthma, autism, bladder cancer, Candidal vaginitis, chronic kidney disease, Crohn's disease, *Clostridium difficile* infection, the common cold, constipation, dementia, dental caries (tooth decay), diabetes mellitus, diverticulosis, eczema, chronic obstructive pulmonary disease (COPD), *Escherichia coli* infection, gastrointestinal tract infections, gastrointestinal inflammation, gum disease, halitosis, *Helicobacter pylori* infection, hepatic encephalopathy, high cholesterol, Huntington's disease, infant colic, infectious childhood diarrhea, infectious diarrhea, inflammatory bowel diseases, irritable bowel syndrome, kidney disease, lactose intolerance, *Listeria monocytogenes* infection, lower respiratory infection, metabolic disorder, multidrug-resistant bacterial infection, necrotizing enterocolitis, neurodegeneration, pancreatitis, pneumonia, obesity, oral disease, Parkinson's disease, pouchitis, radiation-associated diarrhea, respiratory infection, *Salmonella thymurium* infection, sepsis, small intestinal bacteria overgrowth, surgical site infections, traveler's diarrhea, ulcerative colitis, upper respiratory infection, urinary tract infection, vaginal infection, ventilator associated pneumonia, vulvo vaginitis, vulvovaginal candidiasis, yeast infection, or any combination thereof, or conditions associated therewith comprising providing any of the aforementioned compositions such as anyone or more of the deposited strains above to a subject that has been preferably selected or identified as one that would benefit from an adjustment of the gut microbiome and, optionally evaluating or measuring the treatment, amelioration, or inhibition of allergies, infection risk in the critically ill, sexually transmitted infections, acne, acute infectious diarrhea, acute respiratory tract infections, allergic rhinitis, Alzheimer's disease, antibiotic-associated diarrhea, atopic dermatitis, asthma, autism, bladder cancer, Candidal vaginitis, chronic kidney disease, Crohn's disease, *Clostridium difficile* infection, the common cold, constipation, dementia, dental caries (tooth decay), diabetes mellitus, diverticulosis, eczema, *Escherichia coli* infection, gastrointestinal tract infections, gastrointestinal inflammation, gum disease, halitosis, *Helicobacter pylori* infection, hepatic encephalopathy, high cholesterol, Huntington's disease, infant colic, infectious childhood diarrhea, infectious diarrhea, inflammatory bowel diseases, irritable bowel syndrome, kidney disease, lactose intolerance, *Listeria monocytogenes* infection, lower respiratory infection, metabolic disorder, multidrug-resistant bacterial infection, necrotizing enterocolitis, neurodegeneration, pancreatitis, pneumonia, obesity, oral disease, Parkinson's disease, pouchitis, radiation-associated diarrhea, respiratory infection, *Salmonella thymurium* infection, sepsis, small intestinal bacteria overgrowth, surgical site infections, traveler's diarrhea, ulcerative colitis, upper respiratory infection, urinary tract infection, vaginal infection, ventilator associated pneumonia, vulvo vaginitis, vulvovaginal candidiasis, or yeast infection, or any combination thereof, or conditions associated therewith.

Accordingly, it is contemplated that one or more of the compositions disclosed herein are useful as a medicament. In some embodiments, one or more of the compositions disclosed herein such as anyone or more of the deposited strains above are for use in treating acne, acute infectious diarrhea, acute respiratory tract infections, allergic rhinitis, Alzheimer's disease, antibiotic-associated diarrhea, atopic dermatitis, asthma, autism, bladder cancer, Candidal vaginitis, chronic kidney disease, Crohn's disease, *Clostridium difficile* infection, the common cold, constipation, dementia, dental caries (tooth decay), diabetes mellitus, diverticulosis, eczema, chronic obstructive pulmonary disease (COPD), *Escherichia coli* infection, gastrointestinal tract infections, gastrointestinal inflammation, gum disease, halitosis, *Helicobacter pylori* infection, hepatic encephalopathy, high cholesterol, Huntington's disease, infant colic, infectious childhood diarrhea, infectious diarrhea, inflammatory bowel diseases, irritable bowel syndrome, kidney disease, lactose intolerance, *Listeria monocytogenes* infection, lower respiratory infection, metabolic disorder, multidrug-resistant bacterial infection, necrotizing enterocolitis, neurodegeneration, pancreatitis, pneumonia, obesity, oral disease, Parkinson's disease, pouchitis, radiation-associated diarrhea, respiratory infection, *Salmonella thymurium* infection, sepsis, small intestinal bacteria overgrowth, surgical site infections, traveler's diarrhea, ulcerative colitis, upper respiratory infection, urinary tract infection, vaginal infection, ventilator associated pneumonia, vulvo vaginitis, vulvovaginal candidiasis, or yeast infection, or any combination thereof. In some embodiments, the composition is formulated for oral delivery, such as a powder (e.g., a lyophilized powder), a liquid (such as a beverage, which may contain a flavoring), a capsule or a caplet (e.g., a capsule or caplet, which may contain a preservative, antifungal agent, or antibacterial agent), a spray (e.g., an emulsion, microemulsion, or nanoemulsion comprising a fatty acid), or a food.

Embodiments of the present disclosure provided herein are described by way of the following exemplary numbered alternatives:

1. A composition comprising an isolate of *Bacteroides* designated LJ00115, wherein said isolate of *Bacteroides* comprises a 16S rRNA gene sequence encoding or corresponding to at least 95%, 96%, 97%, 98%, 99%, or 100% sequence identity of the rDNA sequence of SEQ ID NO: 1 or the complement thereof, such as the selected isolate of *Bacteroides* designated LJ00115 deposited with the Westerdijk Fungal Biodiversity Institute, CBS collection, at Uppsalalaan 8, 3508 AD UTRECHT, The Netherlands under reference number CBS 149345.

2. A composition comprising an isolate of *Odoribacter* designated LJ00541, wherein said isolate of *Odoribacter* comprises a 16S rRNA gene sequence encoding or corresponding to at least 95%, 96%, 97%, 98%, 99% or 100% sequence identity of the rDNA sequence of SEQ ID NO: 2 or the complement thereof, such as the selected isolate of *Odoribacter* designated LJ00541 deposited with the Westerdijk Fungal Biodiversity Institute, CBS collection, at Uppsalalaan 8, 3508 AD UTRECHT, The Netherlands under reference number CBS 149346.

3. A composition comprising an isolate of *Bacteroides* designated PRB03A2_ANA_TSB_B11, wherein said isolate of *Bacteroides* comprises a 16S rRNA gene sequence encoding or corresponding to at least 95%, 96%, 97%, 98%, 99% or 100% sequence identity of the rDNA sequence of SEQ ID NO: 3 or the complement thereof, such as the selected isolate of *Bacteroides* designated PRB03A2_ANA_TSB_B11 deposited with the Westerdijk Fungal Biodiversity Institute, CBS collection, at Uppsalalaan 8, 3508 AD UTRECHT, The Netherlands under reference number CBS 149347.

4. A composition comprising an isolate of *Parabacteroides* designated PRB02A2_ANA_TSB_F6, wherein said isolate of *Parabacteroides* comprises a 16S rRNA gene sequence encoding or corresponding to at least 95%, 96%, 97%, 98%, 99% or 100% sequence identity of the rDNA sequence of SEQ ID NO: 4 or the complement thereof, such as the selected isolate of *Parabacteroides* designated PRB02A2_ANA_TSB_F6 deposited with the Westerdijk Fungal Biodiversity Institute, CBS collection, at Uppsalalaan 8, 3508 AD UTRECHT, The Netherlands under reference number CBS 149348.

5. A composition comprising an isolate of *Bacteroides* designated PRB01A2_ANA_MRS_C7, wherein said isolate of *Bacteroides* comprises a 16S rRNA gene sequence encoding or corresponding to at least 95%, 96%, 97%, 98%, 99% or 100% sequence identity of the rDNA sequence of SEQ ID NO: 5 or the complement thereof, such as the selected isolate of *Bacteroides* designated PRB01A2_ANA_MRS_C7 deposited with the Westerdijk Fungal Biodiversity Institute, CBS collection, at Uppsalalaan 8, 3508 AD UTRECHT, The Netherlands under reference number CBS 149340.

6. A composition comprising an isolate of *Paraprevotella* designated LJ00262, wherein said isolate of *Paraprevotella* comprises a 16S rRNA gene sequence encoding or corresponding to at least 95%, 96%, 97%, 98%, 99% or 100% sequence identity of the rDNA sequence of SEQ ID NO: 6 or the complement thereof, such as the selected isolate of *Paraprevotella* designated LJ00262 deposited with the Westerdijk Fungal Biodiversity Institute, CBS collection, at Uppsalalaan 8, 3508 AD UTRECHT, The Netherlands under reference number CBS 149341.

7. A composition comprising an isolate of *Coprococcus* designated LJ00622, wherein said isolate of *Coprococcus* comprises a 16S rRNA gene sequence encoding or corresponding to at least 95%, 96%, 97%, 98%, 99%, or 100% sequence identity of the rDNA sequence of SEQ ID NO: 7 or the complement thereof, such as the selected isolate of *Coprococcus* designated LJ00622 deposited with the Westerdijk Fungal Biodiversity Institute, CBS collection, at Uppsalalaan 8, 3508 AD UTRECHT, The Netherlands under reference number CBS 149349.

8. A composition comprising an isolate of *Acidaminococcus* designated PRB01A2_ANA_GAM_C8, wherein said isolate of *Acidaminococcus* comprises a 16S rRNA gene sequence encoding or corresponding to at least 95%, 96%, 97%, 98%, 99% or 100% sequence identity of the rDNA sequence of SEQ ID NO: 8 or the complement thereof, such as the selected isolate of *Acidaminococcus* designated PRB01A2_ANA_GAM_C8 deposited with the Westerdijk Fungal Biodiversity Institute, CBS collection, at Uppsalalaan 8, 3508 AD UTRECHT, The Netherlands under reference number CBS 149342.

9. A composition comprising an isolate of *Bifidobacterium* designated PRB02A2_ANA_TSB_A11, wherein said isolate of *Bifidobacterium* comprises a 16S rRNA gene sequence encoding or corresponding to at least 95%, 96%, 97%, 98%, 99% or 100% sequence identity of the rDNA sequence of SEQ ID NO: 9 or the complement thereof, such as the selected isolate of *Bifidobacterium* designated PRB02A2_ANA_TSB_A11 deposited with the Westerdijk Fungal Biodiversity Institute, CBS collection, at Uppsalalaan 8, 3508 AD UTRECHT, The Netherlands under reference number CBS 149343.

10. A composition comprising an isolate of *Bifidobacterium* designated PRB03A2_ANA_GAM_.Ab_B11 wherein said isolate of *Bifidobacterium* comprises a 16S rRNA gene sequence encoding or corresponding to at least 95%, 96%, 97%, 98%, 99% or 100% sequence identity of the rDNA sequence of SEQ ID NO: 10 or the complement thereof, such as the selected isolate of *Bifidobacterium* designated PRB03A2_ANA_GAM.Ab_B11 is deposited with the Westerdijk Fungal Biodiversity Institute, CBS collection, at Uppsalalaan 8, 3508 AD UTRECHT, The Netherlands under reference number CBS 149344.

11. The composition of any one of alternatives 1-10, further comprising a prebiotic, stabilizer, antibacterial agent, antifungal agent, or media component.

12. The composition of alternative 11, wherein the prebiotic is inulin, fructooligosaccharide, galactooligosaccharide, xylooligosaccharide, or lactulose.

13. The composition of alternative 11, wherein the stabilizer comprises a sugar, a sugar alcohol, an amino acid, a lipid, or any combination thereof.

14. The composition of alternative 13, wherein the stabilizer is glucose, sucrose, trehalose, lactose, maltodextrin, polydextrose, dextran, fructose, oligofructose, cellulose, glycerol, adonitol, inositol, mannitol, sorbitol, gums, hydrolyzed protein, skim milk powder, milk powder, gel beads, raffinose, soybean oligosaccharides, fructooligosaccharides, galactooligosaccharides, galactosyl lactose, palatinose, lactitol, xylitol, sorbitol, mannitol, trehalose, maltose, milk, whey, whey protein concentrates, casein, casein hydrolysates, lactoferrin, lactoperoxidase, lactoglobulins, glycomacropeptides, lacto-saccharides, lacto-lipids, or short chain fatty acids including acetic, propionic, butyric, isobutyric, valeric, isovaleric, or caproic acids or any combination thereof.

15. The composition of alternative 11, wherein the antibacterial agent is bacteriocin, amoxicillin, ampicillin, azithromycin, cefaclor, cefdinir, cefotaxime, ceftazidime, ceftriaxone, cefuroxime, cephalexin, cephalosporin, ciprofloxacin, clarithromycin, clavulanate, clindamycin, clotrimazole, dalbavancin, demeclocycline, dicloxacillin, doxycycline, eravacycline, erythromycin, fluconazole, furazolidone, lansoprazole, levofloxacin, lincomycin, metronidazole, minocycline, moxifloxacin, nitroimidazole, omadacycline, oritavancin, oxacillin, penem, penicillin, penicillin V potassium, rifabutin, sulfamethoxazole, sulfasalazine, telavancin, tetracycline, tinidazole, trimethoprim, or vancomycin, or any combination thereof.

16. The composition of alternative 11, wherein the antifungal agent is amphotericin B, clotrimazole, econazole, fluconazole, itraconazole, ketoconazole, miconazole, natamycin, nystatin, posaconazole, terconazole, terbinafine, or voriconazole, or any combination thereof.

17. The composition of alternative 11, wherein the media component is selected from any one or more of the components set forth in TABLE 2.

18. The composition of alternative 17, wherein the media component further comprises agar.

19. The composition of any one of alternatives 1-18, wherein the isolate or composition or both are lyophilized, spray dried, or freeze-dried.

20. The composition of any one of alternatives 1-19, further comprising at least one additional bacterial population, wherein said at least one additional bacterial population comprises a 16S rRNA gene encoding or corresponding to a sequence selected from any one or more of the rDNA sequences of SEQ ID NOS: 1-10 or the complement thereof or any one or more of a sequence having at least 95%, 96%, 97%, 98%, or 99% sequence identity to any one or more of SEQ ID NOS: 1-10 or the complement thereof.

21. The composition of any one of alternatives 1-20, wherein said composition comprises at least nine additional bacterial populations, wherein each of the at least nine additional bacterial populations comprises a 16S rRNA gene encoding or corresponding to a unique sequence selected from any one or more of the rDNA sequences of SEQ ID NOS: 1-10 or the complement thereof or any one or more of a sequence having at least 95%, 96%, 97%, 98%, or 99% sequence identity to any one or more of SEQ ID NOS: 1-10 or the complement thereof.

22. The composition of any one of alternatives 1-21, further comprising at least one additional bacterial population selected from the bacteria set forth in TABLE 3.

23. A method of treating, ameliorating, preventing, or inhibiting an allergy, infection, sexually transmitted infection, acne, acute infectious diarrhea, acute respiratory tract infections, allergic rhinitis, Alzheimer's disease, antibiotic-associated diarrhea, atopic dermatitis, asthma, autism, bladder cancer, Candidal vaginitis, chronic kidney disease, Crohn's disease, *Clostridium difficile* infection, the common cold, constipation, dementia, dental caries (tooth decay), diabetes mellitus, diverticulosis, eczema, chronic obstructive pulmonary disease (COPD), *Escherichia coli* infection, gastrointestinal tract infections, gastrointestinal inflammation, gum disease, halitosis, *Helicobacter pylori* infection, hepatic encephalopathy, high cholesterol, Huntington's disease, infant colic, infectious childhood diarrhea, infectious diarrhea, inflammatory bowel diseases, irritable bowel syndrome, kidney disease, lactose intolerance, *Listeria monocytogenes* infection, lower respiratory infection, metabolic disorder, multidrug-resistant bacterial infection, necrotizing enterocolitis, neurodegeneration, pancreatitis, pneumonia, obesity, oral disease, Parkinson's disease, pouchitis, radiation-associated diarrhea, respiratory infection, *Salmonella thymurium* infection, sepsis, small intestinal bacteria overgrowth, surgical site infections, traveler's diarrhea, ulcerative colitis, upper respiratory infection, urinary tract infection, vaginal infection, ventilator associated pneumonia, vulvo vaginitis, vulvovaginal candidiasis, yeast infection, or any combination thereof, or conditions associated therewith comprising providing any of the aforementioned compositions of alternatives 1-22 to a subject that has been preferably selected as one that would benefit from an adjustment of the microbiome and, optionally evaluating the treatment, amelioration, or inhibition of said allergy, infection, sexually transmitted infection, acne, acute infectious diarrhea, acute respiratory tract infections, allergic rhinitis, Alzheimer's disease, antibiotic-associated diarrhea, atopic dermatitis, asthma, autism, bladder cancer, Candidal vaginitis, chronic kidney disease, Crohn's disease, *Clostridium difficile* infection, the common cold, constipation, dementia, dental caries (tooth decay), diabetes mellitus, diverticulosis, eczema, *Escherichia coli* infection, gastrointestinal tract infections, gastrointestinal inflammation, gum disease, halitosis, *Helicobacter pylori* infection, hepatic encephalopathy, high cholesterol, Huntington's disease, infant colic, infectious childhood diarrhea, infectious diarrhea, inflammatory bowel diseases, irritable bowel syndrome, kidney disease, lactose intolerance, *Listeria monocytogenes* infection, lower respiratory infection, metabolic disorder, multidrug-resistant bacterial infection, necrotizing enterocolitis, neurodegeneration, pancreatitis, pneumonia, obesity, oral disease, Parkinson's disease, pouchitis, radiation-associated diarrhea, respiratory infection, *Salmonella thymurium* infection, sepsis, small intestinal bacteria overgrowth, surgical site infections, traveler's diarrhea, ulcerative colitis, upper respiratory infection, urinary tract infection, vaginal infection, ventilator associated pneumonia, vulvo vaginitis, vulvovaginal candidiasis, or yeast infection, or any combination thereof, or conditions associated therewith.

24. The composition of any one of alternatives 1-22, for use as a medicament.

25. The composition of any one of alternatives 1-22, for use in treating acne, acute infectious diarrhea, acute respiratory tract infections, allergic rhinitis, Alzheimer's disease, antibiotic-associated diarrhea, atopic dermatitis, asthma, autism, bladder cancer, Candidal vaginitis, chronic kidney disease, Crohn's disease, *Clostridium difficile* infection, the common cold, constipation, dementia, dental caries (tooth decay), diabetes mellitus, diverticulosis, eczema, chronic obstructive pulmonary disease (COPD), *Escherichia coli* infection, gastrointestinal tract infections, gastrointestinal inflammation, gum disease, halitosis, *Helicobacter pylori* infection, hepatic encephalopathy, high cholesterol, Huntington's disease, infant colic, infectious childhood diarrhea, infectious diarrhea, inflammatory bowel diseases, irritable bowel syndrome, kidney disease, lactose intolerance, *Listeria monocytogenes* infection, lower respiratory infection, metabolic disorder, multidrug-resistant bacterial infection, necrotizing enterocolitis, neurodegeneration, pancreatitis, pneumonia, obesity, oral disease, Parkinson's disease, pouchitis, radiation-associated diarrhea, respiratory infection, *Salmonella thymurium* infection, sepsis, small intestinal bacteria overgrowth, surgical site infections, traveler's diarrhea, ulcerative colitis, upper respiratory infection, urinary tract infection, vaginal infection, ventilator associated pneumonia, vulvo vaginitis, vulvovaginal candidiasis, yeast infection, or any combination thereof.

26. The composition of any one of alternatives 1-22, wherein said composition is formulated for oral delivery, such as powder, liquid, capsule, caplet, spray, or food.

DETAILED DESCRIPTION

The compositions and methods described herein are beneficial for reducing the use of antimicrobial and/or antipathogenic compounds in subjects, while at the same time allowing those subjects to be impervious to or capable of remaining healthy when confronted with harmful microbes such as pathogenic bacteria. These benefits may be accomplished by administering to a subject an effective amount of a beneficial, non-pathogenic microorganism or a composition comprising said microorganism as described herein, which will then reduce, inhibit, ameliorate, or mitigate the pathogenic microbial infection. In some embodiments, it is preferred that the formulation administered to the subject comprising the beneficial, non-pathogenic microorganism as described herein also comprises or is administered with (e.g., co-administration) with an effective amount of one or more prebiotics, stabilizers, antibacterial agents, antifungal agents, or media components. Administration of such beneficial, non-pathogenic microorganism as described herein and said prebiotics, stabilizers, antibacterial agents, antifungal agents, and/or media components can be accomplished together or as part of a planned system or method, and administration of both can provide a benefit that may not be available or experienced by the subject that received administration of either alone.

The term "anti-pathogenic," is used herein, in accordance with its ordinary and plain meaning as understood by a person of ordinary skill in the art, which may include an anti-pathogenic compound or composition, which helps to kill, eliminate, or remove an agent of disease such as infectious organisms including bacteria, viruses, and fungi. Antipathogenic compounds or compositions may also include compounds, which help to remove a noninfectious agent of disease such as a chemical or a toxin.

As used herein, treatment of a disease or condition refers to reducing the severity or frequency of at least one symptom of that disease or condition, compared to a similar but untreated patient. Treatment can also refer to halting, slowing, or reversing the progression of a disease or condition, compared to a similar but untreated patient. Treatment may further comprise addressing the root cause of the disease and/or one or more symptoms. Non-limiting examples of diseases or conditions in a subject that may be treated or inhibited by administration of a composition disclosed herein include allergies, infection risk in the critically ill, sexually transmitted infections, acne, acute infectious diarrhea, acute respiratory tract infections, allergic rhinitis, Alzheimer's disease, antibiotic-associated diarrhea, atopic dermatitis, asthma, autism, bladder cancer, Candidal vaginitis, chronic kidney disease, Crohn's disease, *Clostridium difficile* infection, the common cold, constipation, dementia, dental caries (tooth decay), diabetes mellitus, diverticulosis, eczema, chronic obstructive pulmonary disease (COPD), *Escherichia coli* infection, gastrointestinal tract infections, gastrointestinal inflammation, gum disease, halitosis, *Helicobacter pylori* infection, hepatic encephalopathy, high cholesterol, Huntington's disease, infant colic, infectious childhood diarrhea, infectious diarrhea, inflammatory bowel diseases, irritable bowel syndrome, kidney disease, lactose intolerance, *Listeria monocytogenes* infection, lower respiratory infection, metabolic disorder, multidrug-resistant bacterial infection, necrotizing enterocolitis, neurodegeneration, pancreatitis, pneumonia, obesity, oral disease, Parkinson's disease, pouchitis, radiation-associated diarrhea, respiratory infection, *Salmonella thymurium* infection, sepsis, small intestinal bacteria overgrowth, surgical site infections, traveler's diarrhea, ulcerative colitis, upper respiratory infection, urinary tract infection, vaginal infection, ventilator associated pneumonia, vulvo vaginitis, vulvovaginal candidiasis, or yeast infection.

In some embodiments, the composition comprising the beneficial, non-pathogenic microorganism as isolated as described herein provides conditions that support nonpathogenic bacterium viability. For instance, the composition may promote growth and metabolism or may promote a dormant state (e.g., freezing, lyophilization, or freeze drying) from which viable nonpathogenic bacteria can be recovered. When the composition promotes growth or metabolism, it may contain water and/or nutrients that nonpathogenic bacteria consume, e.g., as ammonium, ammonia, urea, oxygen, carbon dioxide, or trace minerals. In some embodiments, the composition comprising nonpathogenic bacteria provides conditions that support beneficial bacteria viability. For instance, the composition may promote growth and metabolism or may promote a dormant state (e.g., freezing, lyophilization, or freeze drying) or storage state as described herein, from which viable beneficial bacteria can be recovered. When the composition promotes growth or metabolism, it may contain water and/or nutrients that beneficial bacteria consume, e.g., as ammonium ions, ammonia, urea, oxygen, carbon dioxide, or trace minerals.

Although described herein primarily with respect to humans, aspects of this disclosure can, in some embodiments, be applied to benefit a subject, which should be interpreted herein to include a livestock animal, a domestic animal, a wild animal, fish, birds, mammals, or humans.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise.

As used herein, "a" or "an" may mean one or more than one.

As used herein, the term "about" or "approximately" has its usual meaning as understood by those skilled in the art and thus indicates that a value includes the inherent variation of error for the method being employed to determine a value, or the variation that exists among multiple determinations.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "function" and "functional" as used herein have their plain and ordinary meaning as understood in light of the specification, and refer to a biological, enzymatic, or therapeutic function.

As used herein, the terms "isolated" or "isolate" have their plain and ordinary meaning as understood in light of the specification, and refer to a substance and/or entity that has been (1) separated from at least some of the components with which it was associated when initially produced (whether in nature and/or in an experimental setting), and/or (2) produced, prepared, and/or manufactured by a human. Isolated substances and/or entities may be separated from equal to, about, at least, at least about, not more than, or not more than about, 10%, 20%, 30%, 40%, 50%, 60%, 70%, 80%, 90%, 95%, 98%, 99%, or 100% of the other components with which they were initially associated (or ranges including and/or spanning the aforementioned values). In some embodiments, isolated agents are, are about, are at least, are at least about, are not more than, or are not more than 80%, 85%, 90%, 91%, 92%, 93%, 94%, 95%, 96%, 97%, 98%, 99%, or 100% pure (or within a range of purity defined by any two of the aforementioned values). As used herein, an organism that is "isolated" may be "pure" (e.g., substantially free of other components). As used herein, the term "isolated cell" may refer to a cell not contained in a multi-cellular organism or tissue.

As used herein, "in vivo" is given its plain and ordinary meaning as understood in light of the specification and refers to the performance of a method inside living organisms, usually animals, mammals, including humans, and plants, or living cells which make up these living organisms, as opposed to a tissue extract or dead organism.

As used herein, "ex vivo" is given its plain and ordinary meaning as understood in light of the specification and refers to the performance of a method outside a living organism with little alteration of natural conditions.

As used herein, "in vitro" is given its plain and ordinary meaning as understood in light of the specification and refers to the performance of a method outside of biological conditions, e.g., in a petri dish or test tube.

The terms "nucleic acid" or "nucleic acid molecule" as used herein have their plain and ordinary meaning as understood in light of the specification, and refer to polynucleotides, such as deoxyribonucleic acid (DNA) or ribonucleic acid (RNA), oligonucleotides, those that appear in a cell naturally, fragments generated by the polymerase chain reaction (PCR), or fragments generated by any of ligation, scission, endonuclease action, or exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. The term "nucleic acid molecule" also includes so-called "peptide nucleic acids," which comprise naturally-occurring or modified nucleic acid bases attached to a polyamide backbone. Nucleic acids can be either single stranded or double stranded. "Oligonucleotide" can be used interchangeable with nucleic acid and can refer to either double stranded or single stranded DNA or RNA. A nucleic acid or nucleic acids can be contained in a nucleic acid vector or nucleic acid construct (e.g. plasmid, virus, retrovirus, lentivirus, bacteriophage, cosmid, fosmid, phagemid, bacterial artificial chromosome (BAC), yeast artificial chromosome (YAC), or human artificial chromosome (HAC)) that can be used for amplification and/or expression of the nucleic acid or nucleic acids in various biological systems. Typically, the vector or construct will also contain elements including but not limited to promoters, enhancers, terminators, inducers, ribosome binding sites, translation initiation sites, start codons, stop codons, polyadenylation signals, origins of replication, cloning sites, multiple cloning sites, restriction enzyme sites, epitopes, reporter genes, selection markers, antibiotic selection markers, targeting sequences, peptide purification tags, or accessory genes, or any combination thereof.

The terms "peptide", "polypeptide", and "protein" as used herein have their plain and ordinary meaning as understood in light of the specification and refer to macromolecules comprised of amino acids linked by peptide bonds. The numerous functions of peptides, polypeptides, and proteins are known in the art, and include but are not limited to enzymes, structure, transport, defense, hormones, or signaling. Peptides, polypeptides, and proteins are often, but not always, produced biologically by a ribosomal complex using a nucleic acid template, although chemical syntheses are also available.

The term "gene" as used herein have their plain and ordinary meaning as understood in light of the specification, and generally refers to a portion of a nucleic acid that encodes a protein or functional RNA; however, the term may optionally encompass regulatory sequences. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as rRNAs, tRNAs and miRNAs. In some cases, the gene includes regulatory sequences involved in transcription, or message production or composition. In other embodiments, the gene comprises transcribed sequences that encode for a protein, polypeptide or peptide. In keeping with the terminology described herein, an "isolated gene" may comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof. As will be understood by those in the art, this functional term "gene" includes both genomic sequences, RNA or cDNA sequences, or smaller engineered nucleic acid segments, including nucleic acid segments of a non-transcribed part of a gene, including but not limited to the non-transcribed promoter or enhancer regions of a gene. Smaller engineered gene nucleic acid segments may express or may be adapted to express using nucleic acid manipulation technology, proteins, polypeptides, domains, peptides, fusion proteins, mutants and/or such like.

Some embodiments described herein relate to pharmaceutical compositions or dietary supplements that comprise, consist essentially of, or consist of an effective amount of any one or more of the cell compositions described herein. Such pharmaceutical compositions and dietary supplements are suitable for human and/or veterinary applications.

The terms "individual", "subject", "host," or "patient" as used herein have their usual meaning as understood by those skilled in the art and thus includes a human or a non-human mammal. The term "mammal" is used in its usual biological sense. Thus, it specifically includes, but is not limited to, primates, including simians (chimpanzees, apes, monkeys), humans, cattle, horses, sheep, goats, swine, rabbits, dogs, cats, rodents, rats, mice, or guinea pigs.

The terms "effective amount" or "effective dose" as used herein have their usual meaning as understood by those skilled in the art and refer to that amount of a recited composition or compound that results in an observable biological effect. Actual dosage levels of active ingredients in an active composition of the presently disclosed subject matter can be varied so as to administer an amount of the active composition or compound that is effective to achieve the desired response for a particular subject and/or application. The selected dosage level will depend upon a variety of factors including, but not limited to, the activity of the composition, formulation, route of administration, combination with other drugs or treatments, severity of the condition being treated, and the physical condition and prior medical history of the subject being treated. In some embodiments, a minimal dose is administered, and dose is escalated in the absence of dose-limiting toxicity to a minimally effective amount. Determination and adjustment of an effective dose, as well as evaluation of when and how to make such adjustments, are contemplated herein.

As used herein, "pharmaceutically acceptable" has its plain and ordinary meaning as understood in light of the specification and refers to carriers, excipients, and/or stabilizers that are nontoxic to the cell or mammal being exposed thereto at the dosages and concentrations employed or that have an acceptable level of toxicity. A "pharmaceutically acceptable" "diluent," "excipient," and/or "carrier" as used herein have their plain and ordinary meaning as understood in light of the specification and are intended to include any and all solvents, dispersion media, coatings, antibacterial or antifungal agents, isotonic or absorption delaying agents, compatible with administration to humans, cats, dogs, or other vertebrate hosts. Typically, a pharmaceutically acceptable diluent, excipient, and/or carrier is a diluent, excipient, and/or carrier approved by a regulatory agency of a Federal, a state government, or other regulatory agency, or listed in the U.S. Pharmacopeia or other generally recognized pharmacopeia for use in animals, including humans as well as non-human mammals, such as cats and dogs. The term diluent, excipient, and/or "carrier" can refer to a diluent, adjuvant, excipient, or vehicle with which the pharmaceutical composition is administered. Such pharmaceutical diluent, excipient, and/or carriers, which can be incorporated in any one or more of the compositions described herein, include sterile liquids, such as water and oils, including those of petroleum, animal, vegetable or synthetic origin. Water, saline solutions or aqueous dextrose and glycerol solutions can be employed as liquid diluents, excipients, and/or carriers. Suitable pharmaceutical diluents and/or excipients, which can be incorporated in any one or more of the compositions described herein, also include starch, glucose, lactose, sucrose, gelatin, malt, rice, flour, chalk, silica gel, sodium stearate, glycerol monostearate, talc, sodium chloride, dried skim milk, glycerol, propylene, glycol, water, or ethanol. The physiologically acceptable carrier may also comprise one or more of the following: antioxidants, such as ascorbic acid, low molecular weight (less than about 10 residues) polypeptides, proteins, such as serum albumin, gelatin, immunoglobulins, hydrophilic polymers such as polyvinylpyrrolidone, amino acids, carbohydrates such as glucose, mannose, or dextrins, chelating agents such as EDTA, sugar alcohols such as mannitol or sorbitol, salt-forming counterions such as sodium, and nonionic surfactants such as TWEEN®, polyethylene glycol (PEG), PLURONICS® or preservatives such as an essential oil, methyl paraben, propyl paraben, or sodium salt of parabens. Preferably, the preservative is bronidiol. The composition, if desired, can also contain minor amounts of wetting, bulking, emulsifying agents, or pH buffering agents. These compositions can take the form of solutions, suspensions, emulsion, sustained release formulations and the like. The formulation should suit the mode of administration.

In some embodiments, the bacterial cells isolated as described herein are frozen or cryopreserved and then thawed or lyophilized or freeze-dried. Freezing or cryopreserving can be done in any conventional matter as a means of prolonging the shelf life of cells. This includes but is not limited to dry ice, liquid nitrogen, or refrigeration. In some embodiments, cryoprotectants are added to the cells prior to freezing.

Cryoprotectants are cell composition additives to improve efficiency and yield of low temperature cryopreservation by preventing formation of large ice crystals. Cryoprotectants include but are not limited to dimethyl sulfoxide (DMSO), ethylene glycol, glycerol, propylene glycol, trehalose, formamide, methyl-formamide, dimethyl-formamide, glycerol 3-phosphate, proline, sorbitol, diethyl glycol, sucrose, triethylene glycol, polyvinyl alcohol, polyethylene glycol, or hydroxyethyl starch. Cryoprotectants can be used as part of a cryopreservation medium, which include other components such as nutrients (e.g. albumin, serum, bovine serum, fetal calf serum [FCS]) to enhance post-thawing survivability of the cells. In these cryopreservation media, at least one cryoprotectant may be found at a concentration that is, is about, is at least, is at least about, is not more than, or is not more than about, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, 80%, or 90%, or any percentage within a range defined by any two of the aforementioned numbers.

Additional excipients with desirable properties include but are not limited to preservatives, adjuvants, stabilizers, solvents, buffers, diluents, solubilizing agents, detergents, surfactants, chelating agents, antioxidants, alcohols, ketones, aldehydes, ethylenediaminetetraacetic acid (EDTA), citric acid, salts, sodium chloride, sodium bicarbonate, sodium phosphate, sodium borate, sodium citrate, potassium chloride, potassium phosphate, magnesium sulfate sugars, dextrose, fructose, mannose, lactose, galactose, sucrose, sorbitol, cellulose, serum, amino acids, polysorbate 20, polysorbate 80, sodium deoxycholate, sodium taurodeoxycholate, magnesium stearate, octylphenol ethoxylate, benzethonium chloride, thimerosal, gelatin, esters, ethers, 2-phenoxyethanol, urea, or vitamins, or any combination thereof. Some excipients may be in residual amounts or contaminants from the process of manufacturing, including but not limited to serum, albumin, ovalbumin, antibiotics, inactivating agents, formaldehyde, glutaraldehyde, β-propiolactone, gelatin, cell debris, nucleic acids, peptides, amino acids, or growth medium components or any combination thereof. The amount of the excipient may be found in the composition at a percentage that is, is about, is at least, is at least about, is not more than, or is not more than about, 0%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 95%, 100% w/w or any percentage by weight in a range defined by any two of the aforementioned numbers.

The term "pharmaceutically acceptable salts" has its plain and ordinary meaning as understood in light of the specification and includes relatively non-toxic, inorganic and organic acid, or base addition salts of compositions or excipients, including without limitation, analgesic agents, therapeutic agents, other materials, and the like. Examples of pharmaceutically acceptable salts, which may be included in any one or more of the formulations comprising the bacteria described herein, include those derived from mineral acids, such as hydrochloric acid and sulfuric acid, and those derived from organic acids, such as ethanesulfonic acid, benzenesulfonic acid, or p-toluenesulfonic acid, and the like. Examples of suitable inorganic bases for the formation of salts include the hydroxides, carbonates, and bicarbonates of ammonia, sodium, lithium, potassium, calcium, magnesium, aluminum, or zinc, and the like. Salts may also be formed with suitable organic bases, including those that are non-toxic and strong enough to form such salts. For example, the class of such organic bases may include but are not limited to mono-, di-, and trialkylamines, including methylamine, dimethylamine, and triethylamine; mono-, di-, or trihydroxyalkylamines including mono-, di-, and triethanolamine; amino acids, including glycine, arginine and lysine; guanidine; N-methylglucosamine; N-methylglucamine; L-glutamine; N-methylpiperazine; morpholine; ethylenediamine; N-benzylphenethylamine; or trihydroxymethyl aminoethane.

Proper formulation is dependent upon the route of administration chosen. Techniques for formulation and administration of the compounds described herein are known to those skilled in the art. Multiple techniques of administering a compound exist in the art including, but not limited to, enteral, oral, rectal, topical, sublingual, buccal, intraaural, epidural, epicutaneous, aerosol, parenteral delivery, including intramuscular, subcutaneous, intra-arterial, intravenous, intraportal, intra-articular, intradermal, peritoneal, intramedullary injections, intrathecal, direct intraventricular, intraperitoneal, intranasal or intraocular injections.

As used herein, a "carrier" has its plain and ordinary meaning as understood in light of the specification and refers to a compound, particle, solid, semi-solid, liquid, or diluent that facilitates the passage, delivery and/or incorporation of a compound to cells, tissues and/or bodily organs.

As used herein, a "diluent" has its plain and ordinary meaning as understood in light of the specification and refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

Administered "in combination," as used herein, means that two (or more) different compositions are delivered to the subject during the course of the subject's affliction with the disorder, e.g., the two or more compositions are delivered after the subject has been diagnosed or selected as one having the disorder and before the disorder has been cured or eliminated. In some embodiments the subject is selected to receive any one or more of the compositions described herein by diagnostic analysis or clinical evaluation or both. For instance, in some embodiments, a subject is screened to determine whether said subject lacks one or more beneficial bacteria or has a reduced amount of said one or more beneficial bacteria prior to receiving an administration of any one or more of the compositions described herein. In some embodiments, the delivery of one therapy is still occurring when the delivery of the second begins, so that there is overlap. This is sometimes referred to herein as "simultaneous" or "concomitant" or "concurrent delivery".

In other embodiments, the delivery of one therapy ends before the delivery of the other therapy begins. This is sometimes referred to herein as "successive" or "sequential delivery." In embodiments of either case, the therapy is more effective because of combined administration. For example, the second therapy is a more effective, e.g., an equivalent effect is seen with less of the second therapy, or the second therapy reduces symptoms to a greater extent, than would be seen if the second therapy were administered in the absence of the first therapy, or the analogous situation is seen with the first therapy. In some embodiments, delivery is such that the reduction in a symptom, or other parameter related to the disorder is greater than what would be observed with one therapy delivered in the absence of the other. The effect of the two therapies can be partially additive, wholly additive, or greater than additive (e.g., synergistic). The delivery can be such that an effect of the first therapy delivered is still detectable when the second is delivered. "Microbiome" as used herein has its plain and ordinary meaning as understood in light of the specification and refers to a population, e.g., one or more microorganisms that live on a surface of a subject, e.g., in the gut, mouth, skin, and/or elsewhere in a subject. The population may have one or more beneficial functions and/or benefits, relevant to supporting the life of a subject. "Metagenome" refers to the collective genomes of a microbiota or microbiome.

In some embodiments, "nonpathogenic bacteria" refers to bacterial strains, which are not known to cause harm. In some embodiments, nonpathogenic bacteria are not known to cause harm, disease, or death to the subject. Nonpathogenic bacteria may include beneficial bacteria. A beneficial bacterium refers to a live bacterium, which may confer a health benefit on the subject. Beneficial bacteria may be associated with a subject's microbiome, e.g., providing a benefit to a subject's microbiome. For example, beneficial bacteria may compete with pathogenic bacteria, e.g., consuming scarce nutrients, or generating byproducts that are harmful to other organisms, e.g., changing a pH level that is not conducive to the undesirable organism's growth. Beneficial bacteria may provide a benefit by delivering a beneficial product or byproduct to the subject, e.g., a product or byproduct which typically inhibits growth or reproduction of pathogenic bacteria. Beneficial bacteria may additionally or alternatively deliver a product or byproduct which promotes growth and metabolism of other beneficial bacteria.

As used herein, compositions may comprise one or multiple isolates of bacteria. These bacteria may include novel strains and species e.g., any one or more of the bacteria, which comprise a 16S rRNA gene encoding or corresponding to a sequence selected from any one or more of the rDNA sequence of SEQ ID NOS: 1-10 or the complement thereof or any one or more of a sequence having at least 95%, 96%, 97%, 98%, or 99% sequence identity to any one or more of SEQ ID NOS: 1-10 or the complement thereof, as well as, strains selected from any one or more of *Absiella, Acetanaerobacterium, Acetatifactor, Acetivibrio, Acetoanaerobium, Acetobacterium, Acholeplasma, Achromobacter, Acidaminococcus, Acidibacillus, Acidiplasma, Acidovorax, Acinetobacter, Actinomyces, Actinomycetaceae, Acutalibacter, Adlercreutzia, Aerococcus, Aeromicrobium, Agathobacter, Agathobaculum, Akkermansi, Algibacter, Algoriella, Algoriphagus, Alicyclobacillus, Alistipes, Alkalibacillus, Alkalibacter, Alkalibacterium, Alkalibaculum, Alkalicoccus, Alkahphilus, Allisonella, Allobaculum, Allofustis, Alloprevotella, Alloscardovia, Alysiella, Aminomonas, Aminomonas, Anaeroarcus, Anaerobacillus, Anaerobacterium, Anaerobium, Anaerobranca, Anaerococcus, Anaeroco-lumna, Anaerofilum, Anaerofustis, Anaeroglobus, Anaerolineaceae, Anaeromassilibacillus, Anaeromicrobium, Anaeromusa, Anaeromyxobacter, Anaerorhabdus, Anaerosalibacter, Anaerosphaera, Anaerosporobacter, Anaerostipes, Anaerotignum, Anaerotruncus, Anaerovibrio, Anaerovorax, Aneurinibacillus, Angelakisella, Apibacter, Aquaspirillum, Arabia, Arachidicoccus, Arcobacter, Arcticibacter, Armatimonadia, Arsenicibacter, Asaccharobacter, Asticcacaulis, Atopobacter, Atopobium, Atribacteria, Auricoccus, Azoarcus, Azospira, Bacillaceae, Bacillus, Bacteroidales, Bacteroides, Bacteroidetes, Bariatricus, Barnesiella, Beduini, Bergeriella, Bernardetia, Bhargavaea, Bifidobacterium, Bilophila, Bittarella, Blattabacterium, Blautia, Bordetella, Borrelia, Brachyspira, Brevibacillus, Brevundimonas, Buchnera, Bulleidia, Burkholderiales, Butyricicoccus, Butyricimonas, Butyrivibrio, Caecibacter, Caenibacillus, Caenispirillum, Caldanaerobacter, Caldanaerobius, Caldibacillus, Caldicellulosiruptor, Caldicoprobacter, Caldisalinibacter, Caldisphaera, Calditerricola, Calditerrivibrio, Caloramator, Caloranaerobacter, Caminibacter, Caminicella, Campylobacter, Candidatus Arsenophonus, Candidatus Arthromitus, Candidatus Babela, Candidatus Blochmannia, Candidatus Carsonella, Candidatus Chrysopegis, Candidatus Cloacimonas, Candidatus Dependentiae, Candidatus Desulforudis, Candidatus Desulfovibrio, Candidatus Dorea, Candidatus Evansia, Candidatus Fonsibacter, Candidatus Frackibacter, Candidatus Gastranaerophilus, Candidatus Gracilibacteria, Candidatus Izimaplasma, Candidatus Kine toplastibacterium, Candidatus Kryptonium, Candidatus Liberibacter, Candidatus Pelagibacter, Candidatus Phytoplasma, Candidatus Profftella, Candidatus Promineofilum, Candidatus Purcelliella, Candidatus Saccharibacteria, Candidatus Soleaferrea, Candidatus Stoquefichus, Candidatus Sukia, Candidatus Symbiothrix, Candidatus Tachikawaea, Capnocytophaga, Carboxydocella, Carboxydothermus, Cardiobacterium, Carnobacterium, Catabacter, Catalinimonas, Catellicoccus, Catenabacterium, Caulobacter, Caviibacter, Cellulomonas, Cellulosilyticum, Centipeda, Cetobacterium, Chishuiella, Chitinophaga, Chlorobaculum, Chlorobium, Christensenella, Chryseobacterium, Cloacibacillus, Clostridia, Clostridiaceae, Clostridiales, Clostridium, Cohnella, Colibacter, Collinsella, Consotaella, Coprobacillus, Coprobacter, Coprococcus, Coriobacteriaceae, Corynebacterium, Criibacterium, Culturomica, Cytophaga, Dakarella, Deferribacter, Defluviitalea, Defluviitoga, Dehalobacter, Deinococcus, Dendrosporobacter, Denitrobacterium, Derxia, Desnuesiella, Desulfallas, Desulfarculus, Desulfitibacter, Desulfitobacterium, Desulfobulbus, Desulfocarbo, Desulfococcus, Desulfocurvus, Desulfofarcimen, Desulfofundulus, Desulfomicrobium, Desulfonatronum, Desulfonauticus, Desulfonispora, Desulfosporosinus, Desulfotomaculum, Desulfovibrio, Desulfovirgula, Desulfurella, Desulfuribacillus, Desulfurispora, Desulfurivibrio, Desulfurobacterium, Desulfuromonas, Dethiobacter, Dethiosulfatibacter, Devosia, Dialister, Dielma, Dinoroseobacter, Domibacillus, Dorea, Draconibacterium, Drancourtella, Dubosiella, Duganella, Duodenibacillus, Dysgonamonadaceae, Dysgonomonas, Effusibacillus, Eggerthella, Ehrlichia, Eikenella, Eisenbergiella, Elizabethkingia, Elusimicrobium, Emergencia, Empedobacter, Emticicia, Endomicrobium, Enorma, Enterobacter, Enterococcus, Enterorhabdus, Enteroscipio, Entomoplasma, Epulopiscium, Ereboglobus, Erysipelatoclostridium, Erysipelothrix, Erysipelotrichaceae, Escherichia, Ethanoligenens, Eubacteriaceae, Eubacterium, Ezakiella, Facklamia, Faecalibacterium, Faecalibaculum, Faecalicatena, Faecalicatena, Faecalimonas,*

*Faecalitalea, Fastidiosipila, Fenollaria, Fermentimonas, Fervidicella, Fervidicola, Fibrobacter, Filifactor, Finegoldia, Firmicutes, Flaviramulus, Flavobacteriaceae, Flavobacterium, Flavonifractor, Floricoccus, Fontibacillus, Formivibrio, Formosa, Fournierella, Francisella, Francisellaceae, Fusibacter, Fusicatenibacter, Fusobacterium, Gabonia, Gabonibacter, Garciella, Gemella, Geminocystis, Gemmiger, Geoalkalibacter, Geobacillus, Geobacter, Geofilum, Geopsychrobacter, Geosporobacter, Gilliamella, Gillisia, Globicatella, Gordonibacter, Gorillibacterium, Gracilibacillus, Granulicatella, Haemophilus, Halanaerobium, Halodesulfovibrio, Halomonas, Halonatronum, Haloplasma, Halothiobacillus, Harryflintia, Helcococcus, Helicobacter, Herbaspirillum, Herbinix, Herminiimonas, Hespellia, Holdemania, Hungateiclostridiaceae, Hungateiclostridium, Hungatella, Hydrogenoanaerobacterium, Hydrogenothermus, Hymenobacter, Ideonella, Idiomarina, Ignavibacterium, Ileibacterium, Ilyobacter, Immundisolibacter, Inediibacterium, Inordinaticella, Intestinibacillus, Intestinibacter, Intestinimonas, Isobaculum, Izhakiella, Jeotgalibaca, Jeotgalicoccus, Jonquetella, Kallipyga, Khelaifiella, Khoudiadiopia, Kineothrix, Kingella, Kiritimatiella, Labilibacter, Labilibaculum, Lachnoanaerobaculum, Lachnobacterium, Lachnoclostridium, Lachnospiraceae, Lachnotalea, Lacinutrix, Lacticigenium, Lactobacillus, Lactococcus, Lactomassilus, Lactonifactor, Lagierella, Laribacter, Lascolabacillus, Lawsonibacter, Lebetimonas, Legionella, Lentibacillus, Leptotrichia, Levyella, Libanicoccus, Lihuaxuella, Listeria, Longilinea, Luteimonas, Luteitalea, Lutibacter, Lutibacter, Lysinibacillus, Macellibacteroides, Mageeibacillus, Magnetofaba, Magnetospirillum, Mahella, Mailhella, Mangrovibacterium, Marasmitruncus, Maribacter, Marinifilaceae, Marinifilum, Marinilabilia, Mariniphaga, Marinitoga, Marinobacter, Marinomonas, Marispirochaeta, Marvinbryantia, Massilibacillus, Massilibacterium, Massilibacteroides, Massilimaliae, Massilioclostridium, Massiliomicrobiota, Mediterranea, Mediterraneibacter, Megamonas, Megasphaera, Melghirimyces, Melioribacter, Melissococcus, Merdibacter, Merdimonas, Mesonia, Mesoplasma, Mesorhizobium, Metaprevotella, Methanobrevibacter, Methanocaldococcus, Methanococcus, Methanosphaera, Methanothermococcus, Methanothermus, Methylomonas, Methylophilales, Millionella, Miniphocibacter, Mitsuokella, Mobilibacterium, Modestobacter, Mogibacterium, Monoglobus, Moorella, Moraxella, Mordavella, Mucilaginibacter, Mucinivorans, Mucispirillum, Murdochiella, Muribaculaceae, Muribaculum, Muricauda, Murimonas, Mycolicibacterium, Mycoplasma, Natranaerobius, Natronincola, Nautilia, Ndongobacter, Negativibacillus, Negativibacillus, Neglecta, Neisseria, Neobitarella, Neofamilia, Niameybacter, Niastella, Novispirillum, Novosphingobium, Oceanibaculum, Oceanicaulis, Oceanicella, Oceanithermus, Oceanivirga, Oceanobacillus, Oceanotoga, Odoribacter, Olsenella, Opitutaceae, Opitutus, Orenia, Oribacterium, Ornithinibacillus, Ornithobacterium, Oscillibacter, Oscillochloris, Oscillospiraceae, Ottowia, Oxalobacter, Paenibacillus, Paludibacter, Parabacteroides, Paraclostridium, Paracoccus, Paraeggerthella, Paraliobacillus, Paramaledivibacter, Paraphotobacterium, Paraprevotella, Parascardovia, Parasporobacterium, Parasutterella, Parvimonas, Paucisalibacillus, Pediococcus, Pedobacter, Pelagibacteraceae, Pelosinus, Peptoanaerobacter, Peptoclostridium, Peptoniphilus, Peptostreptococcaceae, Peptostreptococcus, Perlucidibaca, Persephonella, Petrimonas, Petroclostridium, Petrotoga, Phascolarctobacterium, Phocaeicola, Phocea, Phoenicibacter, Photobacterium, Pilibacter, Piscibacillus, Planifilum, Planococcus, Pleomorphomonas, Polaribacter, Polymorphum, Pontibacillus, Porphyromonadaceae, Porphyromonas, Prevotella, Prevotellaceae, Prevotellamassilia, Prochlorococcus, Prolixibacter, Prolixibacteraceae, Propionispira, Propionispora, Prosthecochloris, Proteiniborus, Proteiniclasticum, Proteiniphilum, Proteocatella, Provencibacterium, Pseudoarcobacter, Pseudobutyrivibrio, Pseudoclostridium, Pseudodesulfovibrio, Pseudoflavonifractor, Pseudomonas, Pseudoramibacter, Pseudoscardovia, Pseudoxanthomonas, Psychrilyobacter, Pustulibacterium, Pygmaiobacter, Pyramidobacter, Raoultibacter, Reyranella, Rhizobium, Rhodobacter, Rhodonellum, Rhodopseudomonas, Rhodothermaceae, Rickettsia, Riemerella, Robiginitalea, Robinsoniella, Romboutsia, Roseburia, Rubneribacter, Rubritepida, Ruminiclostridium, Ruminobacter, Ruminococcaceae, Ruminococcus, Rummeliibacillus, Ruthenibacterium, Saccharibacillus, Saccharicrinis, Salegentibacter, Salibacterium, Salinicoccus, Salisaeta, Sanguibacteroides, Sarcina, Sebaldella, Sedimentibacter, Sedimentisphaera, Sediminibacterium, Selenihalanaerobacter, Selenomonas, Sellimonas, Senegalimassilia, Sharpea, Shewanella, Shigella, Shuttleworthia, Siansivirga, Simplicispira, Sinobaca, Sinomicrobium, Sinorhizobium, Slackia, Sneathia, Solimonas, Solirubrobacter, Solitalea, Solobacterium, Sphingobacterium, Sphingomonas, Spiroplasma, Sporanaerobacter, Sporolactobacillus, Sporolituus, Sporomusa, Staphylococcus, Stomatobaculum, Streptobacillus, Streptococcus, Subdoligranulum, Succinatimonas, Succinispira, Succinivibrionaceae, Sulfuricaulis, Sulfurihydrogenibium, Sulfurimonas, Sulfurivirga, Sutterella, Sutterellaceae, Synechococcus, Synergistes, Syntrophomonas, Syntrophus, Tangfeifania, Tannerella, Tenacibaculum, Tenericutes, Tepidanaerobacter, Tepidibacter, Tepidimicrobium, Tepidimicrobium, Tessaracoccus, Thalassomonas, Thalassospira, Thauera, Thermacetogenium, Thermaerobacter, Thermicanus, Thermincola, Thermithiobacillus, Thermoactinomyces, Thermoanaerobacter, Thermoanaerobacteraceae, Thermoanaerobacterales, Thermoanaerobacterium, Thermobacillus, Thermodesulfobacterium, Thermodesulfobium, Thermodesulfovibrio, Thermohalobacter, Thermophagus, Thermosediminibacter, Thermosinus, Thermosipho, Thermotalea, Thermovenabulum, Thioalkalivibrio, Tidjanibacter, Tindallia, Tissierella, Traorella, Treponema, Trichococcus, Tumebacillus, Turicibacter, Turicimonas, Tyzzerella, Ureaplasma, Urinacoccus, Vagococcus, Vallitalea, Varibaculum, Veillonella, Veillonellaceae, Verrucomicrobium, Victivallales, Victivallis, Virgibacillus, Vogesella, Vukanibacillus, Yersinia, Youngiibacter,* or *Zobellella.*

Compositions may be purified to be substantially free of other organisms or to wherein substantially all of the organisms in the composition are a selected organism or community of organisms. For example, compositions can be purified to a predetermined concentration of nonpathogenic bacteria, live bacteria, isolated species of bacteria, a selected community of species of bacteria, or combinations thereof. Compositions may be purified to exclude a selected organism or community of organisms. For example, compositions disclosed herein may be substantially free of pathogenic bacteria, non-live bacteria, ammonia oxidizing bacteria, or combinations thereof.

In some embodiments, the compositions can further comprise one or more prebiotic, stabilizers, antibacterial agents, antifungal agents, or media components. Usual LAB growth factors or "prebiotics", which has its plain and ordinary meaning as understood in light of the specification, refers to natural growth factors or compounds that induce the growth or activity of microorganisms. Non-limiting examples of prebiotics include skim milk powder (MSK), inulin, fructooligosaccharide, galactooligosaccharide, xylooligosaccharide, lactulose, oligofructose, beta-glucan, isomaltooligosaccharide, guar gum, maltodextrin, arabinooligosaccharide, and resistant starch. Any one or more of the aforementioned prebiotics can be incorporated in any one or more of the compositions described herein. Certain foods are high in prebiotic components, as well, and their contents may be used to enhance the growth or activity of microorganisms. Non-limiting examples of high-prebiotic foods include chicory root, dandelion greens, Jerusalem artichoke, garlic, onions, leeks, asparagus, bananas, barley, oats, apples, konjac root, cocoa, burdock root, flaxseeds, yacon root, jicama root, wheat bran, and seaweed. Any one or more of the aforementioned high-prebiotic foods can be incorporated in any one or more of the compositions described herein.

A "stabilizer" has its plain and ordinary meaning as understood in light of the specification and refers to any compound or material that confers improved stability properties on the one or more microorganism so that probiotics may be developed, stored, and distributed in a wide variety of circumstances while maintaining a useful shelf-life. Non-limiting examples of stabilizers include sugars, sugar alcohols, proteins, amino acids, and fats/lipids. In some embodiments, the stabilizer may be raffinose, soybean oligosaccharides, fructooligosaccharides, galactooligosaccharides, galactosyl lactose, palatinose, lactulose, lactitol, xylitol, sorbitol, mannitol, trehalose, glucose, sucrose, fructose, maltose, milk, milk powders, whey, whey protein concentrates, casein, casein hydrolysates, lactoferrin, lactoperoxidase, lactoglobulins, glycomacropeptides, lactosaccharides, lacto-lipids, or short chain fatty acids including acetic, propionic, butyric, isobutyric, valeric, isovaleric, or caproic acids. Any one or more of the aforementioned stabilizers can be incorporated in any one or more of the compositions described herein.

An "antibacterial agent", also known as an "antibiotic," has its plain and ordinary meaning as understood in light of the specification and refers to a compound or substance with the ability to lower the growth, replication, infection, or spread of bacteria. In some cases, the antibacterial kills the bacteria. Antibacterial agents may be broad spectrum (targeting many species of bacteria) or narrow spectrum (targeting one or few species of bacteria). Many mechanisms of action exist for antibacterial agents, including cell cycle inhibition, disruption of cell surface formation, nutrient uptake inhibition, inhibition of protein synthesis, inhibition of lipid synthesis, inhibition of nucleic acid synthesis, antimetabolic activity, protein-targeting activity, protein degradation, regulation of enzymes, disruption of DNA repair, altering cell surface permeability, and desiccation. Non-limiting examples of antibacterial agents include aminoglycosides, amoxicillin, ampicillin, azithromycin, bacteriocin, bacitracin, beta-lactams, carbapenems, cefaclor, cefdinir, cefotaxime, ceftazidime, ceftriaxone, cefuroxime, cephalexin, cephalosporin, chloramphenicol, ciprofloxacin, clarithromycin, clavulanate, clindamycin, clotrimazole, dalbavancin, demeclocycline, dicloxacillin, doxycycline, eravacycline, erythromycin, fluconazole, furazolidone, lansoprazole, levofloxacin, lincomycin, linezolid, macrolides, metronidazole, minocycline, monobactams, moxifloxacin, nitroimidazole, omadacycline, oritavancin, oxacillin, penem, penicillin, penicillin V potassium, polymyxins, quinolones, rifabutin, rifampin, streptogramins, sulfamethoxazole, sulfasalazine, sulfonamides, telavancin, tetracycline, tinidazole, trimethoprim, or vancomycin. Any one or more of the aforementioned antibiotics can be incorporated in any one or more of the compositions described herein.

An "antifungal agent" has its plain and ordinary meaning as understood in light of the specification and refers to a compound or substance with the ability to lower the growth, replication, infection, or spread of fungi. In some cases, the antifungal agent kills the fungus. Antifungal agents may be broad spectrum (targeting many species of fungi) or narrow spectrum (targeting one or few species of fungi). Many mechanisms of action exist for antifungal agents, including cell cycle inhibition, ergosterol synthesis inhibition, inhibition of heat shock proteins, disruption of spindle and cytoplasmic microtubule function, inhibition of chitin synthesis, disruption of cell surface formation, physicochemical interactions with fungal membrane sterols, nutrient uptake inhibition, inhibition of macromolecular synthesis, inhibition of protein synthesis, inhibition of lipid synthesis, accumulation of squalene, inhibition of nucleic acid synthesis, antimetabolic activity, protein-targeting activity, protein degradation, regulation of enzymes, disruption of DNA repair, altering cell surface permeability, and desiccation. Non-limiting examples of antibacterial agents include amphotericin B, anidulafungin, azoles, benzoic acid, butaconazole, butenafine, capsofungin, ciclopiroxolamine, clotrimazole, econazole, fluconazole, flucyosine, 5-fluorocytosine, griseofulvin, hamycin, isavuconazole, isoconazole, itraconazole, ketoconazole, micafungin, miconazole, naftifine, natamycin, nystatin, pneumocandins, polyenes, posaconazole, ravuconazole, salicylic acid, selenium sulfide, sulconazole, sertaconazole, terconazole, terbinafine, tolnaftate, undecylenic acid, or voriconazole. Any one or more of the aforementioned antifungal agents can be incorporated in any one or more of the compositions described herein.

A "media component", also referred to simply as "media" or "medium," as used herein has its plain and ordinary meaning as understood in light of the specification and refers to a substance that provides nutrients for microorganisms to grow and culture. A media component can either be liquid, or solid through the addition of agar. Media can be classified into the six broad categories: basal media, enriched media, selective media, indicator media, transport media, and storage media. Non-limiting examples of media, a component of which can be included in any one or more of the formulations described herein, include Yeast Peptone Dextrose (YPD), Lysogeny broth (LB), Luria LB, Lennox LB, Miller LB, Synthetic defined growth media (SD), Yeast minimal media (YMM), Yeast nitrogen base (YNB), Minimal salts (M9), Terrific broth, Terrific broth (modified), Hanahan's Broth (SOB Medium), SOC Medium, 2X YT medium, NZCYM Broth, Acetic acid Bacterium Media (AA), *Acetomicrobium faecalis* Media (AF), AATCC Bacteriostasis Media, Blood Heart Infusion Media (BHI), TSA Blood Media, Bifidus Selective Medium Broth (BSM), Fastidious Anaerobe media+blood (FAA), Gifu Anaerobic Broth, Hektoen Enteric Media, Lactobacilli deMan, Rogosa & Sharpe Media, Chopped Meat Media, Mueller-Hinton, Minimal mucin media, Modified Reinforced Clostridial Media, deMan, Rogosa & Sharpe Media, Phenylethyl Alcohol, Reinforced Clostridial Media, Rich Mucin Media, TSB with Hemin and Menadione, Tryptic Soy Broth (TSB), BHI plus Inulin, or Supplemented Brain Heart Infusion. For a listing of desired media components, which can be incorporated into any one or more of the formulations set forth herein, see TABLE 2. Any one or more of the media components of TABLE 2 can be incorporated in any one or more of the compositions described herein and such compositions can be used in any one or more of the methods described herein. In some embodiments, the isolate or composition or both, which may or may not contain any one or more media components, stabilizers, or a prebiotic as described herein, are lyophilized, spray dried, or freeze-dried. This can be performed using any standard method to one skilled in the art.

In some embodiments, the compositions described herein are formulated for oral delivery. Such formulations of the compositions described herein include a powder, liquid, beverage capsule, caplet, spray, or food e.g. those designed for clinical nutrition, a food or beverage supplement or adjuvant designed either for human or animal consumption. Dairy food products or beverages including fermented milks, fresh cheeses or yogurts or their dried or freeze-dried equivalents represent suitable delivery systems or compositions to incorporate any one or more of the bacteria or compositions described herein with or without any one or more of the prebiotics, media components, or stabilizers described herein. As e.g., food supplement or adjuvant powdered milk or milk derivatives matrixes loaded with the selected probiotics proved quite convenient. If ever necessary, said powdered matrixes can be further packaged as e.g. gelatin or cellulose capsules, gelules or tablets. These compositions can further comprise one or more additional lactic acid bacteria and/or further additives, including pH stabilizers, viscosity stabilizers, preservatives, antioxidants, colorants or flavors.

The following examples illustrate only some of the alternatives of the invention and are not intended to constitute any limitation or restriction thereof.

EXAMPLES

Additional embodiments are disclosed in further detail in the following examples, which are not in any way intended to limit the scope of the claims. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Examples 1-2

As disclosed herein, stool samples were collected from healthy human donors at least 18 years of age without acute diseases and infections and without history of major diseases, especially gastrointestinal diseases. The donors were given a self-collecting device and instructions (Fisher Scientific 02-544-208) to collect stool samples. Within 20 minutes from collection, the sample was placed in a refrigerator at 4° C. before processing the same day. Stool samples were processed in an anaerobic chamber. A pea sized sample was taken from inner layers of the stool sample and homogenized using 25 mL of 1×PBS. The stool homogenate was then diluted 1000-fold. Diluted stool homogenate was placed in selective media agar plates inside an anaerobic chamber (TABLE 1).

TABLE 1

List of growth media used in a subset of bacterial isolates, as disclosed herein.

| Strain of Bacterial Isolate | Media |
| --- | --- |
| PRB03A2_ANA_TSB_B11 | TSB |
| PRB03A2_ANA_GAM.Ab_B11 | GAM |
| PRB02A2_ANA_TSB_F6 | TSB |
| PRB02A2_ANA_TSB_A11 | TSB |
| PRB01A2_ANA_MRS_C7 | MRS |
| PRB01A2_ANA_GAM_C8 | GAM |
| LJ00622 | GAMM |
| LJ00541 | BAC |
| LJ00262 | MGAM |
| LJ00115 | BHIS |

The bacteria were allowed to grow at 37° C. for 24-72 hours. Colonies were streaked onto new fresh quad plates using the same media at 37° C. inside an anaerobic chamber for another 24-72 hours. Then this re-streak was repeated two more times. Next, cell pellets were collected and stored in glycerol at −80° C. for future use. Formulations of the media used are outlined in TABLE 2 below. It will be understood that the agar component is optional and used in cases of bacterial growth in solid culture instead bacterial growth in liquid culture.

TABLE 2

Composition of media used for bacterial growth.

| Media (Abbrev) | Reagent | Amount per Liter |
| --- | --- | --- |
| Acetic acid Bacterium Media (AA) | 1) Peptone | 1) 5.0 g |
| | 2) Glucose | 2) 5.0 g |
| | 3) Yeast Extract | 3) 5.0 g |
| | 4) MgSO$_4$ heptahydrate | 4) 1.0 g |
| | 5) Agar | 5) 15 g |
| *Acetomicrobium Faecalis* Media (AF) | 1) Trypticase Peptone | 1) 2.0 g |
| | 2) Yeast Extract | 2) 2.0 g |
| | 3) Glucose | 3) 4.0 g |
| | 4) K$_2$HPO$_4$ | 4) 0.225 g |
| | 5) KH$_2$PO$_4$ | 5) 0.225 g |
| | 6) (NH$_4$)$_2$SO$_4$ | 6) 0.225 g |
| | 7) Sodium chloride | 7) 0.5 g |
| | 8) MgSO$_4$ heptahydrate | 8) 0.1 g |
| | 9) CaCl$_2$ dihydrate | 9) 0.07 g |
| | 10) Sodium acetate | 10) 5.0 g |
| | 11) Vitamin solution | 11) 10 mL |
| | 12) Trace element solution | 12) 10 mL |
| | 13) Resazurin | 13) 1.0 mg |
| | 14) Sodium bicarbonate | 14) 6.0 g |
| | 15) Cysteine-HCl × H2O | 15) 0.5 g |

TABLE 2-continued

Composition of media used for bacterial growth.

| Media (Abbrev) | Reagent | Amount per Liter |
|---|---|---|
| AATCC Bacteriostasis Media | 1) Peptone<br>2) Beef extract<br>3) Sodium chloride<br>4) Agar | 1) 10 g<br>2) 5.0 g<br>3) 5.0 g<br>4) 15 g |
| Blood Heart Infusion Media | 1) Brain extract<br>2) Heart extract<br>3) Proteose peptone<br>4) Sodium chloride<br>5) D(+)-Glucose<br>6) $Na_2HPO_4$<br>7) Agar | 1) 7.8 g<br>2) 9.7 g<br>3) 10 g<br>4) 5.0 g<br>5) 2.0 g<br>6) 2.5 g<br>7) 15 g |
| TSA Blood Media (or Agar) (Blood) | 1) Trypticase Soy Agar with 5% Sheep Blood | 1) Commercially available |
| Bifidus Selective Medium Broth (BSM) | | 1) Commercially available |
| Fastidious Anaerobe media + blood (FAA) | 1) Peptone mix<br>2) Sodium chloride<br>3) Soluble starch<br>4) Agar<br>5) Sodium bicarbonate<br>6) Glucose<br>7) Sodium pyruvate<br>8) Cysteine-HCl × H2O<br>9) Hemin<br>10) Vitamin K<br>11) L-Arginine<br>12) Soluble pyrophosphate<br>13) Sodium succinate<br>14) Defibrinated sheep blood | 1) 23 g<br>2) 5.0 g<br>3) 1.0 g<br>4) 12 g<br>5) 0.4 g<br>6) 1.0 g<br>7) 1.0 g<br>8) 0.5 g<br>9) 0.01 g<br>10) 0.001 g<br>11) 1.0 g<br>12) 0.25 g<br>13) 0.5 g<br>14) 5% |
| Gifu Anaerobic Broth | 1) Peptone<br>2) Soya peptone<br>3) Proteose peptone<br>4) Digested serum<br>5) Yeast extract<br>6) HM peptone B<br>7) HL extract<br>8) Glucose<br>9) $KH_2PO_4$<br>10) Sodium chloride<br>11) Soluble starch<br>12) L-Cysteine hydrochloride<br>13) Sodium thioglycollate | 1) 10 g<br>2) 3.0 g<br>3) 10 g<br>4) 13.5 g<br>5) 5.0 g<br>6) 2.2 g<br>7) 1.2 g<br>8) 3.0 g<br>9) 2.5 g<br>10) 3.0 g<br>11) 5.0 g<br>12) 0.3 g<br>13) 0.3 g |
| Hektoen Enteric Media (or Agar) | | 1) Commercially available |
| Lactobacilli deMan, Rogosa & Sharpe Media (or Agar) | | 1) Commercially available |
| Chopped Meat | 1) Meat extract<br>2) Peptone<br>3) Sodium chloride<br>4) Agar | 1) 10 g<br>2) 10 g<br>3) 5.0 g<br>4) 15 g |
| Mueller-Hinton | 1) Acid hydrolysate of casein<br>2) Beef extract<br>3) Starch<br>4) Agar | 1) 17.5 g<br>2) 2.0 g<br>3) 1.5 g<br>4) 17 g |
| Minimal mucin media | 1) Mucin<br>2) $Na_2HPO_4$<br>3) $KH_2PO_4$<br>4) Ammonium chloride<br>5) Sodium chloride<br>6) Vitamin K<br>7) Mineral trace ATCC mix<br>8) Vitamin mix ATCC solution<br>9) Riboflavin<br>10) L-cysteine hydrochloride<br>11) Noble agar | 1) 3.0 g<br>2) 7.0 g<br>3) 3.0 g<br>4) 1.0 g<br>5) 0.5 g<br>6) 200 uL<br>7) 10 mL<br>8) 10 mL<br>9) 100 mg<br>10) 2.0 g<br>11) 6.0 g |
| Modified Reinforced Clostridial Media | 1) Resazurin solution<br>2) Reinforced clostridial media (or agar) | 1) 4 mL<br>2) Commercially available |
| deMan, Rogosa & Sharpe Agar | 1) Peptone<br>2) Meat extract<br>3) Yeast extract<br>4) D(+)-Glucose<br>5) $K_2HPO_4$<br>6) Sodium acetate trihydrate<br>7) Triammonium citrate<br>8) $MgSO_4$ heptahydrate<br>9) Manganese sulfate tetrahydrate | 1) 10 g<br>2) 8.0 g<br>3) 4.0 g<br>4) 20 g<br>5) 2.0 g<br>6) 5.0 g<br>7) 2.0 g<br>8) 0.2 g<br>9) 0.05 g |

TABLE 2-continued

Composition of media used for bacterial growth.

| Media (Abbrev) | Reagent | Amount per Liter |
| --- | --- | --- |
| Phenylethyl Alcohol | | 1) Commercially available |
| Reinforced Clostridial Agar | 1) Casein enzymatic hydrolysate | 1) 10 g |
| | 2) Beef extract | 2) 10 g |
| | 3) Yeast extract | 3) 3.0 g |
| | 4) Dextrose | 4) 5.0 g |
| | 5) Sodium chloride | 5) 5.0 g |
| | 6) Sodium acetate | 6) 3.0 g |
| | 7) Soluble starch | 7) 1.0 g |
| | 8) L-Cysteine hydrochloride | 8) 0.5 g |
| | 9) Agar | 9) 13.5 g |
| Rich Mucin Media | 1) Beef heart | 1) 5.0 g |
| | 2) Calf brains | 2) 12.5 g |
| | 3) $Na_2HPO_4$ | 3) 2.5 g |
| | 4) D(+)-Glucose | 4) 2.0 g |
| | 5) Peptone | 5) 10 g |
| | 6) Sodium chloride | 6) 5.0 g |
| | 7) Mucin | 7) 2.5 g |
| | 8) Vitamin K solution | 8) 1 mL |
| | 9) Histidine hematin solution | 9) 1 mL |
| | 10) L-cysteine hydrochloride | 10) 2.0 g |
| | 11) Noble agar | 11) 6.0 g |
| TSB with Hemin and Menadione | 1) Hemin | 1) 5 ug/mL |
| | 2) Menadione | 2) 1 ug/mL |
| | 3) Tryptic Soy Broth | 3) Commercially available |
| Tryptic Soy Broth | | 1) Commercially available |
| BHI plus Inulin | | 1) Commercially available |
| Supplemented Brain Heart Infusion | 1) BHI broth | 1) 37 g |
| | 2) Cysteine | 2) 1.0 g |
| | 3) Hemin solution | 3) 10 mL |
| | 4) Resazurin solution (0.1%) | 4) 1 mL |
| | 5) NaCl NaHCO3 solution | 5) 20 mL |
| | 6) Agar | 6) 15 g |
| Tryptone Yeast Extract Glucose Media | 1) Tryptone | 1) 20 g |
| | 2) Yeast extract | 2) 10 g |
| | 3) Glucose | 3) 5.0 g |
| | 4) Cysteine (free base) | 4) 1.0 g |
| | 5) Salts solution A | 5) 40 mL |
| | 6) Hemin solution | 6) 10 mL |
| | 7) Resazurin solution (0.1%) | 7) 1 mL |
| | 8) Agar | 8) 15 g |
| | 9) 10% $NaHCO_3$ | 9) 20 mL |
| Wilkins-Chalgren | 1) Casein enzymic hydrolysate | 1) 10 g |
| | 2) Peptic digest of animal tissue | 2) 10 g |
| | 3) Yeast extract | 3) 5.0 g |
| | 4) Dextrose | 4) 1.0 g |
| | 5) Sodium chloride | 5) 5.0 g |
| | 6) L-Arginine | 6) 1.0 g |
| | 7) Sodium pyruvate | 7) 1.0 g |
| | 8) Hemin | 8) 0.005 g |
| | 9) Menadione | 9) 0.0005 g |
| | 10) Agar | 10) 10 g |
| Bacteroides media | 1) Peptone | 1) 20 g |
| | 2) Soya peptone | 2) 1.5 g |
| | 3) Digested serum | 3) 6.75 g |
| | 4) Liver extract | 4) 0.6 g |
| | 5) Meat extract | 5) 6.15 g |
| | 6) Yeast extract | 6) 10 g |
| | 7) Hemin | 7) 0.003 g |
| | 8) Dextrose | 8) 3.0 g |
| | 9) Sodium chloride | 9) 3.0 g |
| | 10) $KH_2PO_4$ | 10) 2.5 g |
| | 11) Soluble starch | 11) 5.0 g |
| | 12) Bacteroides agar | 12) 0.3 g |
| | 13) Sodium thioglycolate | 13) 0.3 g |
| | 14) Colistin | 14) 1,000,000 units |
| | 15) Neomycin | 15) 0.2 g |
| | 16) Brilliant green | 16) 0.001 g |
| | 17) Agar | 17) 14.7 g |
| GAM, modified | 1) Peptone | 1) 5.0 g |
| | 2) Soya peptone | 2) 3.0 g |
| | 3) Proteose peptone | 3) 5.0 g |
| | 4) Digested serum | 4) 10 g |
| | 5) Yeast extract | 5) 2.5 g |
| | 6) Meat extract | 6) 2.2 g |
| | 7) Liver extract | 7) 1.2 g |
| | 8) Dextrose | 8) 0.5 g |

TABLE 2-continued

Composition of media used for bacterial growth.

| Media (Abbrev) | Reagent | Amount per Liter |
|---|---|---|
| | 9) Soluble starch | 9) 5.0 g |
| | 10) L-Tryptophan | 10) 0.2 g |
| | 11) L-Cysteine hydrochloride | 11) 0.3 g |
| | 12) Sodium thioglycolate | 12) 0.3 g |
| | 13) L-Arginine | 13) 1.0 g |
| | 14) Vitamin K1 | 14) 5.0 mg |
| | 15) Hemin | 15) 10 mg |
| | 16) $KH_2PO_4$ | 16) 2.5 g |
| | 17) Sodium chloride | 17) 3.0 g |
| | 18) Agar | 18) 15 g |
| Modified GAM | 1) Peptone | 1) 10 g |
| | 2) Soya peptone | 2) 3.0 g |
| | 3) Proteose peptone | 3) 10 g |
| | 4) Digested serum | 4) 13.5 g |
| | 5) Yeast extract | 5) 5.0 g |
| | 6) HM peptone B | 6) 2.2 g |
| | 7) HL extract | 7) 1.2 g |
| | 8) Dextrose | 8) 3.0 g |
| | 9) Soluble starch | 9) 5.0 g |
| | 10) L-Cysteine hydrochloride | 10) 0.3 g |
| | 11) Sodium thioglycolate | 11) 0.3 g |
| | 12) Vitamin K1 | 12) 5.0 mg |
| | 13) Hemin | 13) 10 mg |
| | 14) $KH_2PO_4$ | 14) 2.5 g |
| | 15) Sodium chloride | 15) 3.0 g |
| | 16) Agar | 16) 30 g |
| PYG-MEDIUM, modified | | 1) Commercially available |

Examples 3-5

As disclosed herein, the cell pellets grown and isolated from human subject stool samples pursuant to the aforementioned examples, were thawed, then sequenced for variation in the 16S ribosomal RNA gene to identify the species of each pellet. 742 unique strains of bacteria were identified in the human subjects (TABLE 3). Of these, 5 were selected as being particularly enriched in healthy individuals, and these strains were novel isolates, whose 16S genes were <97% identical to known bacteria (TABLE 4). Another 5 were identified as novel isolates, whose 16S genes were <99% identical to known bacteria (TABLE 5).

TABLE 3

List of bacterial isolate strains identified in stool samples, as well as the fraction of samples having this strain with at least 0.001 coverage/prevalence.

| Strain | Prevalence |
|---|---|
| *Bacteroides* sp. 4_3_47FAA | 0.995 |
| *Bacteroides caccae* CL03T12C61 | 0.995 |
| *Parabacteroides* sp. D13 | 0.993 |
| *Bacteroides vulgatus* str. 3775 SL(B) 10 (iv) | 0.993 |
| *Bacteroides* sp. 1_1_30 | 0.989 |
| *Bacteroides* sp. HMSC067B03 | 0.989 |
| *Bacteroides* sp. AF25-17LB | 0.989 |
| *Bacteroides* sp. AM37-9 | 0.989 |
| *Bacteroides* sp. OF03-11BH | 0.989 |
| *Bacteroides* sp. AF32-8BH | 0.989 |
| *Bacteroides uniformis* CL03T00C23 | 0.987 |
| *Bacteroides* sp. HMSC073E02 | 0.987 |
| *Butyricimonas* sp. Marseille-P4593 | 0.987 |
| *Bacteroides* sp. AF20-13LB | 0.987 |
| *Bacteroides thetaiotaomicron* VPI-5482 | 0.985 |
| *Parabacteroides* sp. 2_1_7 | 0.985 |
| *Bacteroides* sp. 2_2_4 | 0.985 |
| *Bacteroides* sp. AF15-14LB | 0.985 |
| *Bacteroides vulgatus* ATCC 8482 | 0.984 |

TABLE 3-continued

List of bacterial isolate strains identified in stool samples, as well as the fraction of samples having this strain with at least 0.001 coverage/prevalence.

| Strain | Prevalence |
|---|---|
| *Bacteroides finegoldii* DSM 17565 | 0.984 |
| *Bacteroides* sp. D22 | 0.984 |
| *Bacteroides ovatus* SD CMC 3f | 0.984 |
| *Parabacteroides merdae* CL03T12C32 | 0.984 |
| *Bacteroides vulgatus* dnLKV7 | 0.984 |
| *Bacteroides ovatus* CL02T12C04 | 0.982 |
| *Bacteroides massiliensis* B84634 = Timone 84634 = DSM 17679 = JCM 13223 | 0.982 |
| *Bacteroides ovatus* | 0.98 |
| *Bacteroides dorei* DSM 17855 | 0.98 |
| *Bacteroides ovatus* CL03T12C18 | 0.978 |
| *Bacteroides caecimuris* | 0.978 |
| *Bacteroides sartorii* | 0.976 |
| *Parabacteroides* sp. SN4 | 0.976 |
| *Bacteroides* sp. AM07-18 | 0.974 |
| *Bacteroides* sp. 2_1_22 | 0.971 |
| *Bacteroides vulgatus* CL09T03C04 | 0.971 |
| *Bacteroides stercoris* CC31F | 0.971 |
| *Alistipes* sp. AF14-19 | 0.971 |
| *Bacteroides* sp. AF25-38AC | 0.971 |
| *Bacteroides uniformis* ATCC 8492 | 0.967 |
| *Parabacteroides* sp. D26 | 0.967 |
| *Mediterranea massiliensis* | 0.967 |
| *Parabacteroides* sp. AM44-16 | 0.967 |
| *Bacteroides eggerthii* 1_2_48FAA | 0.965 |
| *Bacteroides ovatus* 3_8_47FAA | 0.965 |
| *Bacteroides xylanisolvens* CL03T12C04 | 0.965 |
| *Parabacteroides distasonis* CL09T03C24 | 0.963 |
| *Bacteroides* sp. AM16-15 | 0.963 |
| *Bacteroides* sp. AR29 | 0.962 |
| *Bacteroides* sp. D20 | 0.962 |
| *Bacteroides uniformis* str. 3978 T3 i | 0.962 |
| *Bacteroides bouchesdurhonensis* | 0.962 |
| *Bacteroides stercoris* ATCC 43183 | 0.96 |

TABLE 3-continued

List of bacterial isolate strains identified in stool samples, as well as the fraction of samples having this strain with at least 0.001 coverage/prevalence.

| Strain | Prevalence |
|---|---|
| *Bacteroides* sp. 3_1_23 | 0.96 |
| *Bacteroides uniformis* dnLKV2 | 0.96 |
| *Bacteroides* sp. AF39-16AC | 0.96 |
| *Bacteroides finegoldii* CL09T03C10 | 0.958 |
| [*Eubacterium*] *rectale* ATCC 33656 | 0.956 |
| *Oscillibacter* sp. PEA192 | 0.956 |
| *Bacteroides* sp. AM32-11AC | 0.956 |
| *Bacteroides cellulosilyticus* CL02T12C19 | 0.954 |
| *Bacteroides* sp. AF29-11 | 0.954 |
| *Bacteroides* sp. 3_1_19 | 0.952 |
| *Oscillibacter* sp. KLE 1728 | 0.952 |
| *Bacteroides* sp. AM16-13 | 0.952 |
| *Parabacteroides merdae* ATCC 43184 | 0.951 |
| *Bacteroides* sp. AF26-7BH | 0.951 |
| *Parabacteroides* sp. AF27-14 | 0.949 |
| *Bacteroides* sp. AF34-31BH | 0.947 |
| *Parabacteroides distasonis* ATCC 8503 | 0.945 |
| *Alistipes putredinis* DSM 17216 | 0.943 |
| *Bacteroides* sp. 3_1_13 | 0.941 |
| *Bacteroides plebeius* DSM 17135 | 0.938 |
| *Bacteroides coprocola* DSM 17136 | 0.936 |
| *Alistipes shahii* WAL 8301 | 0.936 |
| *Alistipes* sp. AM16-43 | 0.936 |
| *Alistipes finegoldii* DSM 17242 | 0.934 |
| *Roseburia inulinivorans* DSM 16841 | 0.93 |
| *Oscillospiraceae bacterium* VE202-24 | 0.93 |
| *Faecalibacterium* cf. *prausnitzii* KLE1255 | 0.929 |
| *Bacteroides* sp. HMSC068A09 | 0.929 |
| *Bacteroides* sp. KFT8 | 0.925 |
| *Faecalibacterium* sp. AF27-11BH | 0.925 |
| *Faecalibacterium prausnitzii* A2-165 | 0.923 |
| *Parabacteroides* sp. AF19-14 | 0.923 |
| *Bacteroides fragilis* 3_1_12 | 0.921 |
| *Bacteroides* sp. D2 | 0.921 |
| *Faecalibacterium* sp. AM43-5AT | 0.921 |
| *Parabacteroides johnsonii* CL02T12C29 | 0.918 |
| *Bacteroides* sp. AF27-33 | 0.916 |
| *Bacteroides fragilis* str. 3976T8 | 0.914 |
| *Blautia obeum* | 0.912 |
| *Faecalibacterium prausnitzii* M21/2 | 0.912 |
| *Lachnospiraceae bacterium* 7_1_58FAA | 0.91 |
| *Alistipes onderdonkii* WAL 8169 = DSM 19147 | 0.91 |
| *Alistipes obesi* | 0.905 |
| *Faecalibacterium* sp. OM04-11BH | 0.903 |
| *Blautia* sp. Marseille-P2398 | 0.901 |
| *Tannerella* sp. 6_1_58FAA_CT1 | 0.899 |
| *Odoribacter splanchnicus* DSM 20712 | 0.897 |
| *Fusicatenibacter saccharivorans* | 0.897 |
| *Bacteroides fragilis* str. 2-F-2 #4 | 0.897 |
| *Faecalibacterium* sp. OF03-6AC | 0.897 |
| *Clostridiales bacterium* CCNA10 | 0.896 |
| *Faecalibacterium* sp. AF10-46 | 0.892 |
| *Bacteroides* sp. AM23-12 | 0.89 |
| *Roseburia intestinalis* L1-82 | 0.888 |
| *Subdoligranulum* sp. APC924/74 | 0.888 |
| *Bacteroides eggerthii* DSM 20697 | 0.886 |
| *Roseburia faecis* | 0.885 |
| *Faecalibacterium* sp. AF28-13AC | 0.883 |
| *Clostridium* sp. ATCC BAA-442 | 0.872 |
| *Lachnospiraceae bacterium* GAM79 | 0.872 |
| *Parabacteroides distasonis* str. 3776 Po2 i | 0.868 |
| *Prevotella* sp. 109 | 0.868 |
| *Gemmiger formicilis* | 0.866 |
| *Alistipes senegalensis* JC50 | 0.866 |
| *Tannerella* sp. AF04-6 | 0.859 |
| *Bacteroides thetaiotaomicron* dnLKV9 | 0.852 |
| *Roseburia hominis* A2-183 | 0.848 |
| *Bacteroides mediterraneensis* | 0.848 |
| *Roseburia* sp. TF10-5 | 0.844 |
| *Bacteroides cellulosilyticus* | 0.842 |
| *Bacteroides* sp. 2_1_33B | 0.835 |
| *Ruminococcus* sp. AM42-11 | 0.835 |
| *Bacteroides coprophilus* DSM 18228 = JCM 13818 | 0.832 |
| *Bacteroides fluxus* YIT 12057 | 0.832 |
| *Bacteroides intestinalis* DSM 17393 | 0.83 |
| *Ruminococcaceae bacterium* TF06-43 | 0.828 |
| *Bacteroides fragilis* CL05T12C13 | 0.826 |
| *Clostridium* sp. AM34-9AC | 0.826 |
| *Prevotella lascolaii* | 0.824 |
| *Clostridium* sp. AF36-18BH | 0.824 |
| *Culturomica massiliensis* | 0.822 |
| *Clostridium* sp. AF34-10BH | 0.822 |
| *Alistipes* sp. Marseille-P5997 | 0.822 |
| *Parabacteroides johnsonii* DSM 18315 | 0.819 |
| *Ruminococcus* sp. TF11-2AC | 0.819 |
| *Lawsonibacter asaccharolyticus* | 0.817 |
| *Oscillibacter* sp. ER4 | 0.813 |
| *Bacteroides nordii* CL02T12C05 | 0.811 |
| *Parabacteroides* sp. CH2-D42-20 | 0.811 |
| *Bacteroides ndongoniae* | 0.806 |
| *Odoribacter* sp. AF15-53 | 0.804 |
| *Alistipes* sp. AF48-12 | 0.8 |
| *Bacteroides* sp. AF14-46 | 0.799 |
| *Ruminococcaceae bacterium* AF10-16 | 0.795 |
| *Firmicutes bacterium* AF36-3BH | 0.795 |
| *Firmicutes bacterium* AM55-24TS | 0.793 |
| *Clostridium* sp. AF46-12NS | 0.791 |
| *Bacteroides fragilis* HMW 610 | 0.786 |
| *Tannerella* sp. AM09-19 | 0.786 |
| *Paraprevotella clara* YIT 11840 | 0.782 |
| *Bacteroides fragilis* YCH46 | 0.777 |
| [*Eubacterium*] *eligens* ATCC 27750 | 0.777 |
| *Subdoligranulum* sp. 4_3_54A2FAA | 0.777 |
| *Clostridiaceae bacterium* AF18-31LB | 0.775 |
| *Bacteroides faecichinchillae* JCM 17102 | 0.773 |
| *Clostridium* sp. AM22-11AC | 0.773 |
| *Clostridiales bacterium* Choco116 | 0.771 |
| *Bacteroides fragilis* HMW 616 | 0.769 |
| *Bacteroides oleiciplenus* YIT 12058 | 0.767 |
| *Clostridiales bacterium* VE202-03 | 0.767 |
| *Subdoligranulum* sp. OF01-18 | 0.767 |
| *Bacteroides gallinarum* DSM 18171 = JCM 13658 | 0.764 |
| *Firmicutes bacterium* OM08-11AC | 0.764 |
| *Dorea longicatena* DSM 13814 | 0.76 |
| *Coprococcus comes* ATCC 27758 | 0.76 |
| *Ruminococcaceae bacterium* D16 | 0.76 |
| *Bacteroides* sp. AM16-24 | 0.758 |
| *Firmicutes bacterium* TM09-10 | 0.756 |
| *Ruthenibacterium lactatiformans* | 0.755 |
| *Firmicutes bacterium* AM59-13 | 0.749 |
| *Bacteroides acidifaciens* | 0.744 |
| *Firmicutes bacterium* AF22-6AC | 0.742 |
| *Eubacterium* sp. AF22-9 | 0.74 |
| *Firmicutes bacterium* AF16-15 | 0.74 |
| *Firmicutes bacterium* AF36-19BH | 0.74 |
| *Bacteroides galacturonicus* | 0.736 |
| *Bacteroides* sp. OF04-15BH | 0.736 |
| *Dorea formicigenerans* ATCC 27755 | 0.734 |
| *Sanguibacteroides justesenii* | 0.734 |
| [*Clostridium*] *leptum* DSM 753 | 0.731 |
| *Eubacterium* sp. AM46-8 | 0.727 |
| *Anaerotruncus colihominis* DSM 17241 | 0.723 |
| *Bacteroides clarus* YIT 12056 | 0.72 |
| *Butyricicoccus* sp. AM28-25 | 0.72 |
| *Lachnospira pectinoschiza* | 0.718 |
| *Clostridium* sp. M62/1 | 0.712 |
| *Bacteroides congonensis* | 0.712 |
| *Blautia obeum* ATCC 29174 | 0.709 |
| *Eubacterium ventriosum* ATCC 27560 | 0.705 |
| *Prevotellamassilia timonensis* | 0.705 |
| *Eubacterium* sp. AM49-13BH | 0.705 |

TABLE 3-continued

List of bacterial isolate strains identified in stool samples, as well as the fraction of samples having this strain with at least 0.001 coverage/prevalence.

| Strain | Prevalence |
|---|---|
| *Odoribacter* sp. AM16-33 | 0.701 |
| *Clostridiaceae bacterium* TF01-6 | 0.692 |
| *Ruminococcaceae bacterium* AM28-23LB | 0.69 |
| *Lachnospiraceae bacterium* AM48-27BH | 0.69 |
| *Clostridium phoceensis* | 0.689 |
| *Butyricicoccus* sp. AM27-36 | 0.689 |
| *Bacteroides* sp. AF39-11AC | 0.687 |
| *Eubacterium ramulus* ATCC 29099 | 0.683 |
| *Roseburia* sp. OF03-24 | 0.683 |
| *Bacteroides salyersiae* WAL 10018 = DSM 18765 = JCM 12988 | 0.681 |
| *Ruminococcus* sp. AM16-34 | 0.679 |
| *Lactobacillus rogosae* | 0.678 |
| [*Bacteroides*] *pectinophilus* ATCC 43243 | 0.676 |
| *Lachnospiraceae bacterium* 3_1_46FAA | 0.676 |
| *Parabacteroides* sp. TM07-1AC | 0.676 |
| *Bacteroides nordii* WAL 11050 = JCM 12987 | 0.674 |
| *Lachnoclostridium* sp. SNUG30386 | 0.672 |
| *Intestinimonas butyriciproducens* | 0.67 |
| *Dorea formicigenerans* 4_6_53AFAA | 0.665 |
| *Subdoligranulum* sp. AM23-21AC | 0.665 |
| [*Eubacterium*] *hallii* DSM 3353 | 0.661 |
| *Bacteroides togonis* | 0.658 |
| *Subdoligranulum* sp. AM16-9 | 0.658 |
| *Lachnospiraceae bacterium* OF11-28 | 0.658 |
| *Coprococcus catus* | 0.656 |
| *Dorea longicatena* AGR2136 | 0.656 |
| *Ruminococcaceae bacterium* cv2 | 0.656 |
| *Clostridiaceae bacterium* OM08-6BH | 0.654 |
| *Firmicutes bacterium* AF25-13AC | 0.645 |
| *Clostridiales bacterium* KLE1615 | 0.643 |
| *Dorea* sp. AGR2135 | 0.641 |
| *Blautia wexlerae* DSM 19850 | 0.637 |
| *Roseburia* sp. OM04-10AA | 0.636 |
| *Paraprevotella xylaniphila* YIT 11841 | 0.632 |
| *Lachnospiraceae bacterium* 8_1_57FAA | 0.63 |
| *Ruminococcaceae bacterium* KLE1738 | 0.628 |
| *Lachnospiraceae bacterium* 1_1_57FAA | 0.626 |
| *Roseburia* sp. AM23-20 | 0.626 |
| *Parabacteroides goldsteinii* CL02T12C30 | 0.625 |
| *Dorea* sp. Marseille-P4042 | 0.623 |
| *Pseudoflavonifractor* sp. Marseille-P3106 | 0.621 |
| *Parabacteroides* sp. AF17-3 | 0.621 |
| *Tyzzerella* sp. Marseille-P3062 | 0.619 |
| *Blautia massiliensis* | 0.614 |
| *Clostridium* sp. OM08-29 | 0.612 |
| *Butyricicoccus* sp. AM29-23AC | 0.61 |
| *Clostridium* sp. OF03-18AA | 0.61 |
| *Lachnospiraceae bacterium* OM04-12BH | 0.606 |
| *Roseburia* sp. AF25-13LB | 0.603 |
| *Flavonifractor plautii* 1_3_50AFAA | 0.601 |
| *Prevotella stercorea* DSM 18206 | 0.599 |
| *Butyrivibrio crossotus* DSM 2876 | 0.597 |
| *Parabacteroides* sp. AF48-14 | 0.597 |
| *Butyricicoccus* sp. GAM44 | 0.595 |
| *Coprobacter secundus* | 0.59 |
| *Blautia* sp. SG-772 | 0.59 |
| *Alistipes* sp. CHKCI003 | 0.588 |
| *Clostridiaceae bacterium* AF42-6 | 0.586 |
| *Bacteroides* sp. AM10-21B | 0.586 |
| *Subdoligranulum variabile* DSM 15176 | 0.584 |
| *Coprobacillus* sp. AM28-15LB | 0.582 |
| *Burkholderiales bacterium* 1_1_47 | 0.579 |
| *Bacteroides timonensis* | 0.579 |
| *Agathobaculum butyriciproducens* | 0.579 |
| *Barnesiella intestinihominis* YIT 11860 | 0.577 |
| *Parasutterella excrementihominis* YIT 11859 | 0.577 |
| *Ruminococcus* sp. AF16-40 | 0.577 |
| *Intestinimonas massiliensis* | 0.575 |
| *Clostridium* sp. AM49-4BH | 0.575 |
| *Bacteroides stercorirosoris* JCM 17103 | 0.573 |
| *Clostridium* sp. AF36-4 | 0.57 |
| *Burkholderiales bacterium* | 0.568 |
| [*Ruminococcus*] *torques* ATCC 27756 | 0.566 |
| *Ruminococcus bromii* L2-63 | 0.566 |
| *Ruminococcus bicirculans* | 0.564 |
| *Ruminococcus* sp. AM28-29LB | 0.564 |
| *Alistipes timonensis* JC136 | 0.559 |
| *Ruminococcus lactaris* ATCC 29176 | 0.557 |
| *Clostridium* sp. AF37-5 | 0.557 |
| *Bacteroides* sp. 14(A) | 0.555 |
| *Ruminococcus* sp. AF16-50 | 0.555 |
| *Bacteroides ilei* | 0.548 |
| *Parabacteroides* sp. An277 | 0.546 |
| *Angelakisella massiliensis* | 0.544 |
| *Bacteroides cellulosilyticus* DSM 14838 | 0.542 |
| *Blautia* sp. KLE 1732 | 0.542 |
| *Phascolarctobacterium faecium* DSM 14760 | 0.537 |
| *Clostridiaceae bacterium* AF31-3BH | 0.537 |
| *Clostridium* sp. AM34-11AC | 0.535 |
| *Ruminococcus* sp. AF19-15 | 0.531 |
| *Bacteroides salanitronis* DSM 18170 | 0.529 |
| *Ruminococcus* sp. AM28-13 | 0.529 |
| *Butyricimonas virosa* DSM 23226 | 0.522 |
| *Prevotella* sp. Marseille-P4119 | 0.52 |
| *Clostridiaceae bacterium* AF29-16BH | 0.518 |
| *Prevotella* sp. MGM2 | 0.516 |
| *Ruminococcus* sp. AF26-25AA | 0.515 |
| *Flavonifractor plautii* ATCC 29863 | 0.513 |
| *Clostridium* sp. SN20 | 0.513 |
| *Bacteroides* sp. OM08-11 | 0.511 |
| *Ruminococcus* sp. AF17-11 | 0.511 |
| *Ruminococcus* sp. 5_1_39BFAA | 0.509 |
| *Butyricimonas* sp. An62 | 0.509 |
| *Firmicutes bacterium* AM29-6AC | 0.509 |
| *Ruminococcus* sp. AF34-12 | 0.505 |
| *Blautia* sp. AM28-10 | 0.504 |
| *Ruminococcus* sp. OM05-7 | 0.504 |
| *Clostridiales bacterium* AM23-16LB | 0.504 |
| *Tyzzerella nexilis* DSM 1787 | 0.5 |
| *Bacteroides pyogenes* JCM 10003 | 0.5 |
| *Blautia* sp. SF-50 | 0.5 |
| *Clostridiales bacterium* VE202-13 | 0.496 |
| *Alistipes* sp. Marseille-P2431 | 0.496 |
| *Clostridium* sp. AF12-19 | 0.496 |
| [*Eubacterium*] *siraeum* DSM 15702 | 0.495 |
| *Blautia* sp. AF17-9LB | 0.493 |
| *Barnesiella viscericola* DSM 18177 | 0.491 |
| *Ruminococcus faecis* JCM 15917 | 0.491 |
| *Ruminococcus* sp. AF37-20 | 0.491 |
| *Ruminococcus* sp. AM34-10LB | 0.489 |
| *Parabacteroides bouchesdurhonensis* | 0.487 |
| *Parabacteroides* sp. Marseille-P3668 | 0.487 |
| *Ruminococcus* sp. AF43-11 | 0.485 |
| *Butyricicoccus* sp. AF10-3 | 0.484 |
| *Ruminococcus* sp. AM31-32 | 0.484 |
| *Firmicutes bacterium* AF19-2LB | 0.482 |
| *Roseburia* sp. AF20-18LB | 0.482 |
| *Blautia* sp. AM42-2 | 0.478 |
| *Butyricicoccus* sp. AM32-19 | 0.474 |
| *Blautia* sp. AF14-40 | 0.471 |
| *Ruminococcus* sp. AF37-3AC | 0.471 |
| *Akkermansia muciniphila* ATCC BAA-835 | 0.469 |
| *Prevotella* sp. P5-126 | 0.469 |
| *Prevotella* sp. MGM1 | 0.465 |
| *Clostridium* sp. OM05-6BH | 0.465 |
| *Bacteroides* sp. HPS0048 | 0.463 |
| *Roseburia* sp. AF42-8 | 0.463 |
| *Ruminococcus* sp. AM36-18 | 0.462 |
| *Parabacteroides goldsteinii* dnLKV18 | 0.46 |
| *Butyricicoccus* sp. AM05-1 | 0.46 |
| *Ruminococcus* sp. AF17-12 | 0.46 |
| *Ruminococcus* sp. AF42-10 | 0.46 |

TABLE 3-continued

List of bacterial isolate strains identified in stool samples, as well as the fraction of samples having this strain with at least 0.001 coverage/prevalence.

| Strain | Prevalence |
|---|---|
| *Eubacterium* sp. AF15-50 | 0.458 |
| *Blautia* sp. AF19-1 | 0.456 |
| *Pseudoflavonifractor capillosus* ATCC 29799 | 0.454 |
| *Blautia* sp. TM10-2 | 0.454 |
| *Ruminococcus* sp. OM02-16LB | 0.454 |
| [*Clostridium*] *spiroforme* DSM 1552 | 0.452 |
| bacterium LF-3 | 0.451 |
| *Negativibacillus massiliensis* | 0.447 |
| *Clostridiaceae bacterium* AF02-42 | 0.447 |
| *Roseburia* sp. AM16-25 | 0.445 |
| *Butyricicoccus* sp. AF15-40 | 0.445 |
| *Ruminococcus* sp. AF18-29 | 0.445 |
| *Roseburia* sp. AF15-21 | 0.441 |
| *Barnesiella* sp. An22 | 0.44 |
| *Clostridiaceae bacterium* AM27-36LB | 0.44 |
| *Alistipes indistinctus* YIT 12060 | 0.438 |
| *Bacteroides barnesiae* DSM 18169 = JCM 13652 | 0.438 |
| *Bilophila wadsworthia* 3_1_6 | 0.436 |
| *Butyricicoccus* sp. AM18-35 | 0.434 |
| *Bilophila wadsworthia* ATCC 49260 | 0.432 |
| *Blautia* sp. BCRC 81119 | 0.43 |
| *Ruminococcus* sp. AF31-8BH | 0.43 |
| *Clostridium* sp. AF28-12 | 0.43 |
| *Holdemania filiformis* DSM 12042 | 0.427 |
| *Butyricicoccus* sp. AF35-5AC | 0.425 |
| *Eubacterium* sp. AF17-7 | 0.425 |
| *Faecalitalea cylindroides* T2-87 | 0.421 |
| *Bacteroides* sp. An269 | 0.421 |
| *Parabacteroides* sp. AF14-59 | 0.421 |
| *Blautia* sp. AF22-5LB | 0.421 |
| *Ruminococcus* sp. OF05-2BH | 0.421 |
| *Roseburia* sp. AF12-17LB | 0.419 |
| *Ruminococcus* sp. AM31-15AC | 0.419 |
| *Clostridium* sp. AM27-31LB | 0.418 |
| *Ruminococcus* sp. AM43-6 | 0.418 |
| *Ruminococcus* sp. AM54-1NS | 0.418 |
| *Dialister invisus* DSM 15470 | 0.416 |
| *Parabacteroides gordonii* DSM 23371 | 0.416 |
| *Clostridiales bacterium* AF36-10 | 0.414 |
| *Roseburia* sp. OM03-18 | 0.414 |
| *Ruminococcus* sp. AF25-19 | 0.414 |
| *Ruminococcus* sp. AM12-48 | 0.414 |
| *Muribaculaceae bacterium* DSM 103720 | 0.41 |
| *Blautia* sp. OF03-15BH | 0.41 |
| *Clostridia bacterium* UC5.1-2H11 | 0.408 |
| *Erysipelotrichaceae bacterium* GAM147 | 0.408 |
| *Clostridium* sp. TF06-15AC | 0.408 |
| *Ruminococcus* sp. AF17-1AC | 0.408 |
| *Blautia* sp. OF03-13 | 0.407 |
| *Lachnospiraceae bacterium* TM07-2AC | 0.407 |
| *Clostridium* sp. AF27-2AA | 0.405 |
| *Ruminococcus* sp. AM47-2BH | 0.405 |
| *Blautia* sp. OM05-6 | 0.403 |
| *Ruminococcus* sp. AF21-11 | 0.403 |
| *Prevotella* sp. 885 | 0.401 |
| *Clostridium* sp. SS2/1 | 0.399 |
| *Clostridium* sp. AM25-23AC | 0.399 |
| *Parabacteroides chinchillae* | 0.397 |
| *Blautia* sp. AF26-2 | 0.397 |
| *Prevotella* sp. AM42-24 | 0.397 |
| *Ruminococcus* sp. AM26-12LB | 0.397 |
| *Coprobacter fastidiosus* NSB1 | 0.396 |
| *Ruminococcus* sp. AF19-29 | 0.394 |
| *Desulfotomaculum* sp. OF05-3 | 0.392 |
| *Alistipes ihumii* AP11 | 0.388 |
| *Anaeromassilibacillus* sp. Marseille-P3876 | 0.388 |
| *Eubacterium* sp. AF34-35BH | 0.386 |
| *Mediterraneibacter* sp. KCTC 15684 | 0.385 |
| *Lachnospiraceae bacterium* 2_1_58FAA | 0.381 |
| *Ruminococcus* sp. OM04-4AA | 0.381 |
| *Blautia* sp. AF34-10 | 0.379 |
| *Neglecta timonensis* | 0.377 |
| *Monoglobus pectinilyticus* | 0.377 |
| *Dorea* sp. AM58-8 | 0.375 |
| *Clostridium* sp. AF02-29 | 0.375 |
| *Bacteroides* sp. An19 | 0.374 |
| *Eubacterium* sp. OM08-24 | 0.374 |
| *Ruminococcus* sp. TM09-4 | 0.374 |
| *Clostridium* sp. AM33-3 | 0.372 |
| *Blautia* sp. OM07-19 | 0.372 |
| *Roseburia* sp. AF02-12 | 0.372 |
| *Ruminococcus callidus* ATCC 27760 | 0.368 |
| *Blautia* sp. AF32-4BH | 0.364 |
| *Fournierella massiliensis* | 0.363 |
| *Clostridium* sp. AM30-24 | 0.363 |
| *Firmicutes bacterium* OM04-13BH | 0.355 |
| *Prevotella* sp. P4-51 | 0.353 |
| *Odoribacter laneus* YIT 12061 | 0.352 |
| *Anaeromassilibacillus* sp. An250 | 0.352 |
| *Clostridium* sp. AF43-10 | 0.352 |
| *Clostridium* sp. AM46-21 | 0.352 |
| *Clostridium* sp. AF37-5AT | 0.35 |
| [*Ruminococcus*] *gnavus* CC55 001C | 0.348 |
| *Neobitarella massiliensis* | 0.348 |
| *Dorea* sp. AF36-15AT | 0.348 |
| *Bifidobacterium adolescentis* L2-32 | 0.344 |
| *Phocea massiliensis* | 0.344 |
| *Blautia* sp. AF25-12LB | 0.344 |
| *Clostridium* sp. AF15-49 | 0.341 |
| *Erysipelotrichaceae bacterium* 6_1_45 | 0.339 |
| *Prevotella* sp. TF12-30 | 0.339 |
| *Clostridium* sp. AF24-2LB | 0.339 |
| *Clostridium* sp. AF27-5AA | 0.339 |
| *Clostridia bacterium* UC5.1-2F7 | 0.337 |
| *Intestinibacillus* sp. Marseille-P4005 | 0.332 |
| *Blautia* sp. AF19-10LB | 0.33 |
| *Clostridium* sp. AM27-28 | 0.33 |
| *Clostridium* sp. AT4 | 0.328 |
| *Prevotella* sp. P3-122 | 0.328 |
| *Ruminococcus* sp. OM06-36AC | 0.328 |
| *Collinsella aerofaciens* ATCC 25986 | 0.326 |
| *Bifidobacterium stercoris* JCM 15918 | 0.326 |
| *Blautia* sp. AM16-16B | 0.324 |
| *Clostridium* sp. AF20-7 | 0.324 |
| *Collinsella* sp. TF05-9AC | 0.321 |
| *Clostridium* sp. TF11-13AC | 0.321 |
| *Blautia* sp. OM06-15AC | 0.319 |
| *Ruminococcus* sp. OM07-7 | 0.319 |
| *Tidjanibacter massiliensis* | 0.317 |
| *Clostridium* sp. AM45-5 | 0.317 |
| *Anaerotignum lactatifermentans* DSM 14214 | 0.315 |
| *Bacteroides* sp. An51A | 0.315 |
| *Ruminococcus* sp. AM27-11LB | 0.315 |
| *Coprococcus* sp. AF38-1 | 0.315 |
| *Bilophila* sp. 4_1_30 | 0.313 |
| *Ruminococcus* sp. AM23-1 | 0.313 |
| *Prevotella* sp. AM23-5 | 0.311 |
| *Firmicutes bacterium* AF12-30 | 0.31 |
| *Blautia* sp. TF10-30 | 0.308 |
| *Ruminococcus* sp. AF33-11BH | 0.308 |
| *Bifidobacterium longum* NCC2705 | 0.306 |
| *Alistipes* sp. Marseille-P5061 | 0.306 |
| [*Clostridium*] *bolteae* ATCC BAA-613 | 0.304 |
| *Clostridiaceae bacterium* OF09-1 | 0.302 |
| *Firmicutes bacterium* AM10-47 | 0.302 |
| *Bifidobacterium adolescentis* ATCC 15703 | 0.299 |
| *Bifidobacterium longum* subsp. *longum* JCM 1217 | 0.297 |
| *Bifidobacterium adolescentis* DSM 20087 | 0.297 |

TABLE 3-continued

List of bacterial isolate strains identified in stool samples, as well as the fraction of samples having this strain with at least 0.001 coverage/prevalence.

| Strain | Prevalence |
|---|---|
| *Clostridium* sp. AM42-36 | 0.297 |
| *Ruminococcus* sp. AF25-17 | 0.297 |
| *Ruminococcus* sp. AM34-9LB | 0.297 |
| *Collinsella* sp. 4_8_47FAA | 0.295 |
| *Bifidobacterium longum* subsp. *longum* 44B | 0.295 |
| *Alistipes* sp. An54 | 0.295 |
| *Blautia* sp. AF19-13LB | 0.295 |
| *Blautia* sp. AF19-34 | 0.295 |
| *Lachnospiraceae bacterium* 5_1_63FAA | 0.293 |
| *Prevotella bivia* DSM 20514 | 0.293 |
| *Clostridia bacterium* UC5.1-1D10 | 0.293 |
| *Clostridium* sp. AF32-12BH | 0.291 |
| *Prevotella copri* DSM 18205 | 0.289 |
| *Prevotella* sp. P2-180 | 0.289 |
| *Ruminococcus* sp. AF17-22AC | 0.289 |
| *Ruminococcus* sp. B05 | 0.289 |
| *Porphyromonas* sp. COT-108 OH2963 | 0.288 |
| *Mordavella* sp. Marseille-P3756 | 0.288 |
| *Firmicutes bacterium* AM43-11BH | 0.288 |
| *Anaerostipes hadrus* DSM 3319 | 0.286 |
| *Coprococcus* sp. AF16-5 | 0.286 |
| *Ruminococcus* sp. AF20-12LB | 0.286 |
| *Clostridium* sp. L2-50 | 0.284 |
| *Sutterella wadsworthensis* 3_1_45B | 0.284 |
| [*Clostridium*] *symbiosum* WAL-14163 | 0.282 |
| *Sutterella wadsworthensis* HGA0223 | 0.28 |
| *Oscillibacter* sp. PC13 | 0.28 |
| *Prevotella* sp. P3-120 | 0.28 |
| *Blautia* sp. AM23-13AC | 0.28 |
| *Clostridium* sp. AF50-3 | 0.28 |
| *Butyricicoccus* sp. AM42-5AC | 0.278 |
| *Dorea* sp. OM02-2LB | 0.278 |
| *Clostridium* sp. AF23-8 | 0.278 |
| *Ruminococcus* sp. AF27-11AA | 0.278 |
| *Ruminococcus* sp. AM45-2 | 0.278 |
| *Clostridium* sp. 7_3_54FAA | 0.277 |
| *Clostridium* sp. OF09-36 | 0.275 |
| *Lachnoclostridium* sp. SNUG30099 | 0.273 |
| *Ruminococcaceae bacterium* AM07-15 | 0.273 |
| *Blautia* sp. AM29-29 | 0.267 |
| *Clostridium* sp. AF29-8BH | 0.267 |
| *Ruminococcus* sp. AF12-5 | 0.267 |
| *Clostridium* sp. AF20-17LB | 0.266 |
| *Blautia* sp. TF11-31AT | 0.266 |
| *Ruminococcus* sp. AM54-14NS | 0.266 |
| *Ruminococcus* sp. AF14-10 | 0.264 |
| *Ruminococcus* sp. AF45-4BH | 0.26 |
| *Prevotella* sp. AM34-19LB | 0.26 |
| *Lachnospiraceae bacterium* AM21-21 | 0.26 |
| *Faecalibacterium* sp. An122 | 0.258 |
| *Alistipes* sp. An66 | 0.258 |
| *Gabonia massiliensis* | 0.256 |
| *Lachnospiraceae bacterium* AM10-38 | 0.255 |
| *Asaccharobacter celatus* | 0.253 |
| *Pseudoflavonifractor* sp. An184 | 0.251 |
| *Lachnospiraceae bacterium* TF01-11 | 0.249 |
| *Lachnoclostridium* sp. SNUG30370 | 0.247 |
| *Clostridium* sp. AM09-51 | 0.247 |
| *Ruminococcus* sp. AF25-28AC | 0.245 |
| *Ruminococcus* sp. AM36-17 | 0.244 |
| *Anaeromassilibacillus* sp. Marseille-P4683 | 0.242 |
| *Parabacteroides timonensis* | 0.24 |
| *Muribaculum* sp. An287 | 0.24 |
| *Coprococcus* sp. AF16-22 | 0.24 |
| *Coprococcus eutactus* ATCC 27759 | 0.238 |
| *Clostridiales bacterium* VE202-27 | 0.238 |
| *Clostridium* sp. AM42-4 | 0.238 |
| *Bacteroides helcogenes* P 36-108 | 0.236 |
| *Ruminococcus* sp. AM36-2AA | 0.236 |
| *Pediococcus acidilactici* D3 | 0.234 |
| *Mediterranea* sp. An20 | 0.234 |
| *Rikenella microfusus* DSM 15922 | 0.233 |
| *Prevotella* sp. P4-76 | 0.233 |
| *Lachnotalea* sp. AF33-28 | 0.233 |
| *Akkermansia* sp. KLE1605 | 0.231 |
| *Prevotella* sp. P5-108 | 0.231 |
| *Coprococcus* sp. AF19-8AC | 0.229 |
| [*Ruminococcus*] *gnavus* AGR2154 | 0.227 |
| *Ruminococcus* sp. AF21-42 | 0.225 |
| *Lachnospiraceae bacterium* AM26-1LB | 0.225 |
| *Blautia* sp. Marseille-P3087 | 0.223 |
| *Faecalibacterium* sp. An192 | 0.223 |
| [*Clostridium*] *bolteae* 90A9 | 0.222 |
| *Bacteroides* sp. AF16-49 | 0.222 |
| *Clostridium* sp. OF09-10 | 0.222 |
| *Alistipes inops* | 0.22 |
| *Barnesiella* sp. An55 | 0.22 |
| *Ruminococcus* sp. AM29-12LB | 0.22 |
| *Romboutsia timonensis* | 0.218 |
| *Fusicatenibacter* sp. 2789STDY5834925 | 0.218 |
| *Pseudoflavonifractor* sp. AF19-9AC | 0.218 |
| *Ruminococcus champanellensis* 18P13 = JCM 17042 | 0.216 |
| *Haemophilus* sp. HMSC061E01 | 0.216 |
| *Ruminococcus* sp. AF46-10NS | 0.214 |
| *Ruminococcus* sp. AM49-10BH | 0.214 |
| *Ruminococcus* sp. OF02-6 | 0.214 |
| *Bifidobacterium pseudocatenulatum* DSM 20438 = JCM 1200 = LMG 10505 | 0.212 |
| *Flavonifractor* sp. An306 | 0.211 |
| *Blautia wexlerae* AGR2146 | 0.209 |
| [*Clostridium*] *glycyrrhizinilyticum* JCM 13369 | 0.209 |
| *Massilioclostridium coli* | 0.207 |
| *Eubacterium* sp. 3_1_31 | 0.205 |
| *Prevotella buccalis* DNF00985 | 0.205 |
| *Flavonifractor* sp. An135 | 0.203 |
| *Haemophilus* sp. HMSC068C11 | 0.201 |
| *Roseburia* sp. AM59-24XD | 0.201 |
| *Ruminococcus* sp. AM22-14LB | 0.201 |
| *Ruminococcus* sp. AM46-18 | 0.201 |
| *Haemophilus* sp. HMSC71H05 | 0.2 |
| *Clostridium* sp. AF35-15 | 0.198 |
| *Dorea* sp. AF24-7LB | 0.198 |
| *Ruminococcus* sp. OM08-7 | 0.196 |
| *Clostridium* sp. AF21-20LB | 0.196 |
| *Streptococcus thermophilus* JIM 8232 | 0.194 |
| *Eubacterium* sp. TM06-47 | 0.194 |
| *Clostridium* sp. AM16-23 | 0.19 |
| *Ruminococcus* sp. AM32-17LB | 0.19 |
| *Ruminococcus* sp. OM08-9BH | 0.19 |
| *Prevotella bivia* DNF00320 | 0.189 |
| [*Clostridium*] *aldenense* | 0.187 |
| *Ruminococcaceae bacterium* D5 | 0.187 |
| *Butyricicoccus pullicaecorum* 1.2 | 0.185 |
| *Coprobacillus* sp. AF31-1BH | 0.185 |
| *Ruminococcus* sp. AM57-5 | 0.185 |
| *Parabacteroides goldsteinii* DSM 19448 = WAL 12034 | 0.183 |
| *Firmicutes bacterium* OM07-11 | 0.183 |
| *Acidaminococcus intestini* RyC-MR95 | 0.181 |
| *Sutterella wadsworthensis* 2_1_59BFAA | 0.181 |
| *Holdemania* sp. Marseille-P2844 | 0.181 |
| *Lachnospiraceae bacterium* Choco86 | 0.181 |
| *Adlercreutzia equolifaciens* DSM 19450 | 0.179 |
| *Bacteroidales bacterium* KA00344 | 0.179 |
| *Clostridium* sp. OM05-5BH | 0.179 |
| *Ruminococcus* sp. AF24-16 | 0.179 |
| *Anaeromassilibacillus* sp. Marseille-P3371 | 0.178 |
| *Coprobacillus cateniformis* | 0.176 |
| [*Clostridium*] *clostridioforme* 2_1_49FAA | 0.176 |

TABLE 3-continued

List of bacterial isolate strains identified in stool samples, as well as the fraction of samples having this strain with at least 0.001 coverage/prevalence.

| Strain | Prevalence |
|---|---|
| *Lachnospiraceae bacterium* OF09-6 | 0.176 |
| *Clostridium* sp. ATCC 29733 | 0.174 |
| *Prevotella* sp. P4-65 | 0.174 |
| *Ruminococcus* sp. AM33-14 | 0.174 |
| *Haemophilus* sp. HMSC066D02 | 0.172 |
| *Anaeromassilibacillus* sp. An172 | 0.172 |
| *Flavonifractor* sp. An91 | 0.17 |
| *Firmicutes bacterium* AM31-12AC | 0.17 |
| *Clostridium* sp. AM18-55 | 0.17 |
| *Bifidobacterium longum* subsp. *longum* JDM301 | 0.168 |
| *Roseburia* sp. OM02-15 | 0.168 |
| *Holdemanella biformis* DSM 3989 | 0.167 |
| *Haemophilus parainfluenzae* ATCC 33392 | 0.167 |
| *Haemophilus* sp. CCUG 60358 | 0.167 |
| *Metaprevotella massiliensis* | 0.165 |
| *Lachnospiraceae bacterium* AM25-27 | 0.165 |
| *Ruminococcus* sp. AM27-16 | 0.165 |
| *Phascolarctobacterium succinatutens* YIT 12067 | 0.163 |
| *Eggerthella* sp. 1_3_56FAA | 0.163 |
| *Prevotella buccalis* ATCC 35310 | 0.163 |
| *Clostridiales bacterium* VE202-16 | 0.163 |
| *Parabacteroides* sp. AM08-6 | 0.163 |
| *Collinsella* sp. AF25-2LB | 0.163 |
| *Clostridium* sp. AF34-13 | 0.161 |
| *Faecalibacterium* sp. An121 | 0.159 |
| *Bifidobacterium longum* subsp. *suis* | 0.158 |
| [*Clostridium*] *clostridioforme* 90A7 | 0.158 |
| *Collinsella* sp. AF28-5AC | 0.158 |
| *Lachnospiraceae bacterium* TF10-8AT | 0.156 |
| *Coprococcus* sp. OM04-5BH | 0.156 |
| *Haemophilus parainfluenzae* T3T1 | 0.154 |
| *Prevotella ihumii* | 0.154 |
| *Parabacteroides* sp. 426-9 | 0.154 |
| *Eubacterium* sp. AM28-29 | 0.154 |
| *Coprobacillus* sp. AF13-15 | 0.154 |
| *Ruminococcus* sp. AF32-2AC | 0.154 |
| *Bifidobacterium catenulatum* DSM 16992 = JCM 1194 = LMG 11043 | 0.15 |
| *Bifidobacterium bifidum* PRL2010 | 0.15 |
| *Parabacteroides* sp. AF18-52 | 0.15 |
| *Collinsella* sp. AM34-10 | 0.15 |
| *Erysipelotrichaceae bacterium* 2_2_44A | 0.148 |
| [*Clostridium*] *lavalense* | 0.148 |
| *Eggerthella lenta* DSM 2243 | 0.148 |
| *Holdemania massiliensis* AP2 | 0.148 |
| *Flavonifractor* sp. An100 | 0.148 |
| *Victivallales bacterium* CCUG 44730 | 0.148 |
| *Dielma fastidiosa* | 0.147 |
| *Flavonifractor* sp. An10 | 0.147 |
| *Gemmiger* sp. An50 | 0.147 |
| *Gemmiger* sp. An87 | 0.147 |
| *Butyricimonas* sp. Marseille-P3923 | 0.147 |
| *Christensenella minuta* | 0.145 |
| *Faecalitalea cylindroides* ATCC 27803 | 0.145 |
| [*Clostridium*] *asparagiforme* DSM 15981 | 0.143 |
| *Haemophilus* sp. HMSC61B11 | 0.143 |
| *Achromobacter* sp. ATCC35328 | 0.143 |
| *Bacteroides* sp. An279 | 0.143 |
| *Coprobacillus* sp. AF21-8LB | 0.143 |
| *Anaeromassilibacillus* sp. An200 | 0.141 |
| *Ruminococcus* sp. AF42-9BH | 0.141 |
| *Ruminococcaceae bacterium* | 0.139 |
| *Ruminococcus* sp. AF41-9 | 0.139 |
| *Clostridium* sp. AF12-41 | 0.139 |
| *Lachnospiraceae bacterium* AM40-2BH | 0.139 |
| *Clostridium* sp. Marseille-P3244 | 0.137 |
| *Collinsella* sp. AM38-1BH | 0.136 |
| *Alistipes* sp. An116 | 0.134 |
| *Lachnoclostridium* sp. An14 | 0.134 |
| *Flavonifractor* sp. An82 | 0.134 |
| *Dorea* sp. Marseille-P4003 | 0.134 |
| *Ruminococcus* sp. AF19-4LB | 0.134 |
| *Absiella dolichum* DSM 3991 | 0.132 |
| *Hungatella hathewayi* DSM 13479 | 0.13 |
| *Haemophilus parainfluenzae* HK262 | 0.13 |
| *Haemophilus* sp. HMSC073C03 | 0.13 |
| *Eubacterium coprostanoligenes* | 0.128 |
| *Anaerotruncus rubiinfantis* | 0.128 |
| *Anaerofilum* sp. An201 | 0.128 |
| *Ruminococcus* sp. AF14-5 | 0.128 |
| *Eisenbergiella massiliensis* | 0.126 |
| *Lachnoclostridium edouardi* | 0.126 |
| *Enterobacter* sp. EC-NT1 | 0.126 |
| *Clostridium* sp. AF17-2 | 0.126 |
| *Coprobacillus* sp. TF10-10 | 0.126 |
| *Ruminococcus* sp. AF31-14BH | 0.126 |
| *Lachnospiraceae bacterium* 3_1_57FAA_CT1 | 0.125 |
| *Lachnospiraceae bacterium* OM02-26 | 0.125 |
| *Blautia hydrogenotrophica* DSM 10507 | 0.123 |
| *Ruminococcus* sp. AM58-7XD | 0.123 |
| *Lachnospiraceae bacterium* AM23-7LB | 0.123 |
| *Ruminococcus* sp. AM40-10AC | 0.123 |
| *Clostridium* sp. OM07-10AC | 0.121 |
| *Odoribacter* sp. OF09-27XD | 0.121 |
| *Erysipelotrichaceae bacterium* 5_2_54FAA | 0.117 |
| *Prevotella melaninogenica* D18 | 0.117 |
| *Candidatus Stoquefichus* sp. KLE1796 | 0.117 |
| *Blautia* sp. Marseille-P3201T | 0.117 |
| *Clostridium* sp. AF15-31 | 0.117 |
| *Alloprevotella tannerae* ATCC 51259 | 0.115 |
| *Veillonella rogosae* JCM 15642 | 0.115 |
| *Anaerotruncus* sp. AT3 | 0.114 |
| *Clostridium* sp. OF10-22XD | 0.114 |
| *Escherichia coli* O83:H1 str. NRG 857C | 0.112 |
| [*Clostridium*] *innocuum* 2959 | 0.112 |
| *Veillonella* sp. AF42-16 | 0.112 |
| *Erysipelotrichaceae bacterium* AF19-24AC | 0.112 |
| *Coprobacillus* sp. 8_1_38FAA | 0.11 |
| *Turicibacter* sp. H121 | 0.11 |
| *Gordonibacter pamelaeae* 7-10-1-b | 0.108 |
| *Methanobrevibacter smithii* TS145A | 0.108 |
| *Clostridium* sp. KLE 1755 | 0.108 |
| *Eubacterium* sp. TM05-53 | 0.108 |
| *Ruminococcus* sp. AM18-15 | 0.108 |
| *Lachnospiraceae bacterium* AM25-17 | 0.108 |
| *Acetivibrio ethanolgignens* | 0.106 |
| *Prevotella* sp. P5-92 | 0.106 |
| *Catenibacterium mitsuokai* DSM 15897 | 0.104 |
| *Blautia hansenii* DSM 20583 | 0.104 |
| *Escherichia coli* O25b:H4 | 0.104 |
| *Bifidobacterium kashiwanohense* JCM 15439 = DSM 21854 | 0.104 |
| *Clostridia bacterium* UC5.1-1D1 | 0.104 |
| *Bacteroides* sp. An322 | 0.104 |
| *Bacteroides* sp. Marseille-P3684 | 0.104 |
| *Dialister* sp. Marseille-P5638 | 0.104 |
| *Lachnospiraceae bacterium* OF09-33XD | 0.104 |
| *Ruminococcus* sp. AF25-23LB | 0.104 |
| *Coprobacillus* sp. 8_2_54BFAA | 0.103 |
| *Clostridium* sp. FS41 | 0.103 |
| *Anaerotruncus* sp. 22A2-44 | 0.103 |
| *Butyricimonas* sp. Marseille-P2440 | 0.101 |
| *Bifidobacterium* sp. N4G05 | 0.101 |
| *Coprobacillus* sp. AF17-11AC | 0.101 |

TABLE 4

List of strains whose 16S genes were <97% identical to known bacteria.
Strains PRB01A2_ANA_MRS_C7 and PRB01A2_ANA_GAM_C8 were sequenced
using Whole Genome Sequencing. Other strains were sequenced using Sanger sequencing.

| Strain | 16S length | Closest Known Bacterial Species | Identity to Known Species | SEQ ID NO: |
|---|---|---|---|---|
| PRB01A2_ANA_MRS_C7 | 798 | *Bacteroides salyersiae* WAL 10018 = DSM 18765 = JCM 12988 | 96.9% | 5 |
| LJ00262 | 601 | *Paraprevotella xylaniphila* YIT 11841 | 96.1% | 6 |
| PRB01A2_ANA_GAM_C8 | 421 | *Acidaminococcus intestini* RyC-MR95 | 95.9% | 8 |
| PRB02A2_ANA_TSB_A11 | 315 | *Bifidobacterium adolescentis* DSM 20087 | 95.2% | 9 |
| PRB03A2_ANA_GAM.Ab_B11 | 203 | *Bifidobacterium adolescentis* ATCC 15703 | 96.5% | 10 |

TABLE 5

List of strains whose 16S genes were <99% identical to known bacteria. 16S rRNA
gene sequences and corresponding rDNA sequences were determined through Sanger sequencing.

| Strain | 16S length | Closest Known Bacterial Species | Identity to Known Species | SEQ ID NO: |
|---|---|---|---|---|
| LJ00115 | 1392 | *Bacteroides* sp. HMSC068A09 | 98.98% | 1 |
| LJ00541 | 797 | *Odoribacter* sp. AF15-53 | 98.03% | 2 |
| PRB03A2_ANA_TSB_B11 | 576 | *Bacteroides* sp. 4_3_47FAA | 98.61% | 3 |
| PRB02A2_ANA_TSB_F6 | 530 | *Parabacteroides* sp. CH2-D42-20 | 97.34% | 4 |
| LJ00622 | 1357 | *Coprococcus comes* ATCC 27758 | 98.98% | 7 |

What is claimed is:

1. A composition comprising an isolate of *Bifidobacterium* designated PRB03A2_ANA_GAM.Ab_B11, wherein said isolate of *Bifidobacterium* comprises a 16S rRNA gene sequence encoding or corresponding to at least 98% sequence identity of the rDNA sequence of SEQ ID NO: 10 or the complement thereof, wherein the isolate or composition or both are lyophilized, or freeze-dried.

2. The composition of claim 1, wherein the composition further comprises at least one bacteria selected from:
   a) an isolate of *Bacteroides* designated LJ00115, wherein said isolate of *Bacteroides* comprises a 16S rRNA gene sequence encoding or corresponding to at least 99% sequence identity of the rDNA sequence of SEQ ID NO: 1 or the complement thereof;
   b) an isolate of *Odoribacter* designated LJ00541, wherein said isolate of *Odoribacter* comprises a 16S rRNA gene sequence encoding or corresponding to at least 98% sequence identity of the rDNA sequence of SEQ ID NO: 2 or the complement thereof;
   c) an isolate of *Bacteroides* designated PRB03A2_ANA_TSB_B11, wherein said isolate of *Bacteroides* comprises a 16S rRNA gene sequence encoding or corresponding to at least 99% sequence identity of the rDNA sequence of SEQ ID NO: 3 or the complement thereof;
   d) an isolate of *Parabacteroides* designated PRB02A2_ANA_TSB_F6, wherein said isolate of *Parabacteroides* comprises a 16S rRNA gene sequence encoding or corresponding to at least 97% sequence identity of the rDNA sequence of SEQ ID NO: 4 or the complement thereof;
   e) an isolate of *Bacteroides* designated PRB01A2_ANA_MRS_C7, wherein said isolate of *Bacteroides* comprises a 16S rRNA gene sequence encoding or corresponding to at least 97% sequence identity of the rDNA sequence of SEQ ID NO: 5 or the complement thereof;
   f) an isolate of *Paraprevotella* designated LJ00262, wherein said isolate of *Paraprevotella* comprises a 16S rRNA gene sequence encoding or corresponding to at least 96% sequence identity of the rDNA sequence of SEQ ID NO: 6 or the complement thereof;
   g) an isolate of *Coprococcus* designated LJ00622, wherein said isolate of *Coprococcus* comprises a 16S rRNA gene sequence encoding or corresponding to at least 99% sequence identity of the rDNA sequence of SEQ ID NO: 7 or the complement thereof;
   h) an isolate of *Acidaminococcus* designated PRB01A2_ANA_GAM_C8, wherein said isolate of *Acidaminococcus* comprises a 16S rRNA gene sequence encoding or corresponding to at least 96% sequence identity of the rDNA sequence of SEQ ID NO: 8 or the complement thereof; or
   i) an isolate of *Bifidobacterium* designated PRB02A2_ANA_TSB_A11, wherein said isolate of *Bifidobacterium* comprises a 16S rRNA gene sequence encoding or corresponding to at least 95% sequence identity of the rDNA sequence of SEQ ID NO: 9 or the complement thereof.

3. The composition of claim 1, wherein the isolate of *Bifidobacterium* is an isolate of *Bifidobacterium* designated PRB03A2_ANA_GAM.Ab_B11, deposited with the Westerdijk Fungal Biodiversity Institute, CBS collection, at Uppsalalaan 8, 3508 AD UTRECHT, The Netherlands under reference number CBS 149344.

4. The composition of claim 1, wherein the composition further comprises at least one bacteria selected from:
   a) an isolate of *Bacteroides* designated LJ00115, deposited with the Westerdijk Fungal Biodiversity Institute, CBS collection, at Uppsalalaan 8, 3508 AD UTRECHT, The Netherlands under reference number CBS 149345;
   b) an isolate of *Odoribacter* designated LJ00541, deposited with the Westerdijk Fungal Biodiversity Institute, CBS collection, at Uppsalalaan 8, 3508 AD UTRECHT, The Netherlands under reference number CBS 149346;
   c) an isolate of *Bacteroides* designated PRB03A2_ANA_TSB_B11, deposited with the Westerdijk Fungal Biodiversity Institute, CBS collection, at Uppsalalaan 8, 3508 AD UTRECHT, The Netherlands under reference number CBS 149347;
   d) an isolate of *Parabacteroides* designated PRB02A2_ANA_TSB_F6, deposited with the Westerdijk Fungal Biodiversity Institute, CBS collection, at Uppsalalaan 8, 3508 AD UTRECHT, The Netherlands under reference number CBS 149348;
   e) an isolate of *Bacteroides* designated PRB01A2_ANA_MRS_C7, deposited with the Westerdijk Fungal Biodiversity Institute, CBS collection, at Uppsalalaan 8, 3508 AD UTRECHT, The Netherlands under reference number CBS 149340;
   f) an isolate of *Paraprevotella* designated LJ00262, deposited with the Westerdijk Fungal Biodiversity Institute, CBS collection, at Uppsalalaan 8, 3508 AD UTRECHT, The Netherlands under reference number CBS 149341;
   g) an isolate of *Coprococcus* designated LJ00622, deposited with the Westerdijk Fungal Biodiversity Institute, CBS collection, at Uppsalalaan 8, 3508 AD UTRECHT, The Netherlands under reference number CBS 149349;
   h) an isolate of *Acidaminococcus* designated PRB01A2_ANA_GAM_C8, deposited with the Westerdijk Fungal Biodiversity Institute, CBS collection, at Uppsalalaan 8, 3508 AD UTRECHT, The Netherlands under reference number CBS 149342; or i) an isolate of *Bifidobacterium* designated PRB02A2_ANA_TSB_A11, deposited with the Westerdijk Fungal Biodiversity Institute, CBS collection, at Uppsalalaan 8, 3508 AD UTRECHT, The Netherlands under reference number CBS 149343.

5. The composition of claim 1, further comprising a cryoprotectant.

6. The composition of claim 5, wherein the cryoprotectant is selected from sucrose, lactose, trehalose, or dimethyl sulfoxide.

7. The composition of claim 1, further comprising inulin.

8. The composition of claim 1, wherein the composition further comprises a sugar.

9. The composition of claim 8, wherein the sugar is raffinose, soybean oligosaccharides, fructooligosaccharides, galactooligosaccharides, galactosyl lactose, palatinose, lactulose, lactitol, xylitol, sorbitol, mannitol, trehalose, glucose, sucrose, fructose, maltose, or combination thereof.

10. The composition of claim 1, wherein said composition is formulated for oral delivery.

11. The composition of claim 1, wherein said isolate or composition or both is formulated in a powder, liquid, capsule, caplet, spray, or food.

12. A composition comprising an isolate of *Bifidobacterium* designated PRB03A2_ANA_GAM.Ab_B11, wherein said isolate of *Bifidobacterium* comprises a 16S rRNA gene sequence encoding or corresponding to at least 98% sequence identity of the rDNA sequence of SEQ ID NO: 10 or the complement thereof, wherein the isolate or composition or both further comprises:

an antibacterial agent, selected from amoxicillin, ampicillin, azithromycin, cefaclor, cefdinir, cefotaxime, ceftazidime, ceftriaxone, cefuroxime, cephalexin, cephalosporin, ciprofloxacin, clarithromycin, clavulanate, clindamycin, clotrimazole, dalbavancin, demeclocycline, dicloxacillin, doxycycline, eravacycline, fluconazole, furazolidone, lansoprazole, levofloxacin, metronidazole, minocycline, moxifloxacin, nitroimidazole, omadacycline, oritavancin, oxacillin, penem, penicillin V potassium, rifabutin, sulfamethoxazole, sulfasalazine, telavancin, tinidazole, or trimethoprim, or any combination thereof;

an antifungal agent, selected from amphotericin B, clotrimazole, econazole, fluconazole, itraconazole, ketoconazole, miconazole, natamycin, posaconazole, terconazole, terbinafine, or voriconazole, or any combination thereof;

a preservative, selected from sodium salt of parabens or bronidiol;

a cryoprotectant selected from ethylene glycol, propylene glycol, diethyl glycol, triethylene glycol, polyvinyl alcohol, polyethylene glycol, or hydroxyethyl starch or any combination thereof; or an excipient selected from ethylenediaminetetraacetic acid, polysorbate 20, polysorbate 80, magnesium stearate, octylphenol ethoxylate, benzethonium chloride, thimerosal, 2-phenoxyethanol or any combination thereof.

13. The composition of claim 12, wherein the composition further comprises at least one bacteria selected from:

a) an isolate of *Bacteroides* designated LJ00115, wherein said isolate of *Bacteroides* comprises a 16S rRNA gene sequence encoding or corresponding to at least 99% sequence identity of the rDNA sequence of SEQ ID NO: 1 or the complement thereof;

b) an isolate of *Odoribacter* designated LJ00541, wherein said isolate of *Odoribacter* comprises a 16S rRNA gene sequence encoding or corresponding to at least 98% sequence identity of the rDNA sequence of SEQ ID NO: 2 or the complement thereof;

c) an isolate of *Bacteroides* designated PRB03A2_ANA_TSB_B11, wherein said isolate of *Bacteroides* comprises a 16S rRNA gene sequence encoding or corresponding to at least 99% sequence identity of the rDNA sequence of SEQ ID NO: 3 or the complement thereof;

d) an isolate of *Parabacteroides* designated PRB02A2_ANA_TSB_F6, wherein said isolate of *Parabacteroides* comprises a 16S rRNA gene sequence encoding or corresponding to at least 97% sequence identity of the rDNA sequence of SEQ ID NO: 4 or the complement thereof;

e) an isolate of *Bacteroides* designated PRB01A2_ANA_MRS_C7, wherein said isolate of *Bacteroides* comprises a 16S rRNA gene sequence encoding or corresponding to at least 97% sequence identity of the rDNA sequence of SEQ ID NO: 5 or the complement thereof;

f) an isolate of *Paraprevotella* designated LJ00262, wherein said isolate of *Paraprevotella* comprises a 16S rRNA gene sequence encoding or corresponding to at least 96% sequence identity of the rDNA sequence of SEQ ID NO: 6 or the complement thereof;

g) an isolate of *Coprococcus* designated LJ00622, wherein said isolate of *Coprococcus* comprises a 16S rRNA gene sequence encoding or corresponding to at least 99% sequence identity of the rDNA sequence of SEQ ID NO: 7 or the complement thereof;

h) an isolate of *Acidaminococcus* designated PRB01A2_ANA_GAM_C8, wherein said isolate of *Acidaminococcus* comprises a 16S rRNA gene sequence encoding or corresponding to at least 96% sequence identity of the rDNA sequence of SEQ ID NO: 8 or the complement thereof; or i) an isolate of *Bifidobacterium* designated PRB02A2_ANA_TSB_A11, wherein said isolate of *Bifidobacterium* comprises a 16S rRNA gene sequence encoding or corresponding to at least 95% sequence identity of the rDNA sequence of SEQ ID NO: 9 or the complement thereof.

14. The composition of claim 12, wherein the isolate of *Bifidobacterium* is an isolate of *Bifidobacterium* designated PRB03A2_ANA_GAM.Ab_B11, deposited with the Westerdijk Fungal Biodiversity Institute, CBS collection, at Uppsalalaan 8, 3508 AD UTRECHT, The Netherlands under reference number CBS 149344.

15. The composition of claim 12, wherein the composition further comprises at least one bacteria selected from:

a) an isolate of *Bacteroides* designated LJ00115, deposited with the Westerdijk Fungal Biodiversity Institute, CBS collection, at Uppsalalaan 8, 3508 AD UTRECHT, The Netherlands under reference number CBS 149345;

b) an isolate of *Odoribacter* designated LJ00541, deposited with the Westerdijk Fungal Biodiversity Institute, CBS collection, at Uppsalalaan 8, 3508 AD UTRECHT, The Netherlands under reference number CBS 149346;

c) an isolate of *Bacteroides* designated PRB03A2_ANA_TSB_B11, deposited with the Westerdijk Fungal Biodiversity Institute, CBS collection, at Uppsalalaan 8, 3508 AD UTRECHT, The Netherlands under reference number CBS 149347;

d) an isolate of *Parabacteroides* designated PRB02A2_ANA_TSB_F6, deposited with the Westerdijk Fungal Biodiversity Institute, CBS collection, at Uppsalalaan 8, 3508 AD UTRECHT, The Netherlands under reference number CBS 149348;

e) an isolate of *Bacteroides* designated PRB01A2_ANA_MRS_C7, deposited with the Westerdijk Fungal Biodiversity Institute, CBS collection, at Uppsalalaan 8, 3508 AD UTRECHT, The Netherlands under reference number CBS 149340;

f) an isolate of *Paraprevotella* designated LJ00262, deposited with the Westerdijk Fungal Biodiversity Institute, CBS collection, at Uppsalalaan 8, 3508 AD UTRECHT, The Netherlands under reference number CBS 149341;

g) an isolate of *Coprococcus* designated LJ00622, deposited with the Westerdijk Fungal Biodiversity Institute, CBS collection, at Uppsalalaan , 3508 AD UTRECHT, The Netherlands under reference number CBS 149349;

h) an isolate of *Acidaminococcus* designated PRB01A2_ANA_GAM_C8, deposited with the Westerdijk Fungal Biodiversity Institute, CBS collection, at Uppsalalaan 8, 3508 AD UTRECHT, The Netherlands under reference number CBS 149342; or i) an isolate of *Bifidobacterium* designated PRB02A2_ANA_TSB_A11, deposited with the Westerdijk Fungal Biodiversity Institute, CBS collection, at Uppsalalaan 8, 3508 AD UTRECHT, The Netherlands under reference number CBS 149343.

16. The composition of claim 12, further comprising a cryoprotectant.

17. The composition of claim 16, wherein the cryoprotectant is selected from sucrose, lactose, trehalose, or dimethyl sulfoxide.

18. The composition of claim 12, further comprising inulin.

19. The composition of claim 12, wherein the composition further comprises a sugar.

20. The composition of claim 19, wherein the sugar is raffinose, soybean oligosaccharides, fructooligosaccharides, galactooligosaccharides, galactosyl lactose, palatinose, lactulose, lactitol, xylitol, sorbitol, mannitol, trehalose, glucose, sucrose, fructose, maltose, or combination thereof.

21. The composition of claim 12, wherein said composition is formulated for oral delivery.

22. The composition of claim 12, wherein said isolate or composition or both is formulated in a powder, liquid, capsule, caplet, spray, or food.

* * * * *